（12）United States Patent
Harrison et al.

(10) Patent No.: US 9,156,853 B2
(45) Date of Patent: Oct. 13, 2015

(54) AKT INHIBITOR COMPOUNDS FOR TREATMENT OF CANCER

(71) Applicant: ALMAC DISCOVERY LIMITED, Craigavon (GB)

(72) Inventors: Timothy Harrison, Craigavon (GB); Colin O'Dowd, Craigavon (GB); Steven Shepherd, Craigavon (GB); Graham Trevitt, Craigavon (GB); Lixin Zhang, Craigavon (GB); Frank Burkamp, Craigavon (GB)

(73) Assignee: ALMAC DISCOVERY LIMITED, Craigavon (GB)

(*) Notice: Subject to any disclaimer, the term of this patent is extended or adjusted under 35 U.S.C. 154(b) by 0 days.

(21) Appl. No.: 14/387,000

(22) PCT Filed: Mar. 25, 2013

(86) PCT No.: PCT/GB2013/050771
§ 371 (c)(1),
(2) Date: Sep. 22, 2014

(87) PCT Pub. No.: WO2013/140189
PCT Pub. Date: Sep. 26, 2013

(65) Prior Publication Data
US 2015/0045377 A1    Feb. 12, 2015

(30) Foreign Application Priority Data
Mar. 23, 2012  (GB) .................................. 1205164.5

(51) Int. Cl.
C07D 495/04    (2006.01)
C07D 487/04    (2006.01)
C07D 491/048   (2006.01)

(52) U.S. Cl.
CPC ............ *C07D 495/04* (2013.01); *C07D 487/04* (2013.01); *C07D 491/048* (2013.01)

(58) Field of Classification Search
None
See application file for complete search history.

(56) References Cited

FOREIGN PATENT DOCUMENTS

WO    2010088177 A1    8/2010
WO    2011055115 A1    5/2011
WO    2011077098 A1    6/2011

OTHER PUBLICATIONS

Morgan et al., Targeted therapy for Advanced Prostate Cancer: Inhibition of the PI3K/Akt/mTOR pathway. Current Cancer Drug Target. 2009, 9, 237-249.*
Sangai et al., Biomarkers of Response to Akt inhibitor MK-2206 in Breast Cancer. Clinical Cancer Research. 2012, 18, 5816-5828.*
Sawah et al., Perifosine, an AKT inhibitor, modulates ovarian cancer cell line sensitivity to cisplatin-induced growth arrest. Gynecologic Oncology, 2013, 131, 207-212.*
Shafer, S., Kolkhof, P. Failure is an option: learning from unsuccessful proof-of-concept trials. Drug Discovery Today. Nov. 2008, 13, 913-916.*
Horig, H., Pullman, W. From bench to clinic and back: Perspective on the 1st IQPC Translational Research conference. Journal of Translational Medicine. Dec. 2004, 2, 44.*
CAPLUS printout of Foreign Application Publication No. WO2013078254.*
International Search Report and Written Opinion of the International Searching Authority for PCT/GB2013/050771, dated Jun. 28, 2013 (12 pages).

* cited by examiner

*Primary Examiner* — Michael Barker
*Assistant Examiner* — Po-Chih Chen
(74) *Attorney, Agent, or Firm* — Lathrop & Gage LLP; Brian C. Trinque

(57) ABSTRACT

The present invention relates to compounds that are useful as inhibitors of the activity of one or more isoforms of the serine/threonine kinase, AKT. The present invention also relates to pharmaceutical compositions comprising these compounds and to methods of using these compounds in the treatment of cancer and methods of treating cancer.

23 Claims, No Drawings

AKT INHIBITOR COMPOUNDS FOR TREATMENT OF CANCER

RELATED APPLICATIONS

This application is a 35 U.S.C. §371 filing of International Application No. PCT/GB2013/050771, filed Mar. 25, 2013, which claims priority to Great Britain Application No. 1205164.5, filed Mar. 23, 2012, each of which is incorporated herein by reference in its entirety.

The present invention relates to compounds that are useful as inhibitors of the activity of one or more isoforms of the serine/threonine kinase, AKT. The present invention also relates to pharmaceutical compositions comprising these compounds and to methods of using these compounds in the treatment of cancer and methods of treating cancer.

BACKGROUND TO THE INVENTION

The AKT protein family, also known as protein kinases B (PKB), are known to be involved in a wide variety of biological processes including cell proliferation, differentiation, apoptosis, tumorigenesis, as well as glycogen synthesis and glucose uptake. These enzymes are members of the serine/threonine-specific protein kinase family.

The PKB/AKT pathway has been identified as an important regulator of cell survival signalling and apoptosis in cells. Signalling is thought to occur through a range of growth factor receptors including platelet derived growth factor, insulin growth factor and nerve growth factor, resulting in activation of phosphatidylinositol 3-OH kinase (PI-3K). This activation in turn leads to the generation of phosphatidylinositol (3,4,5) triphosphate (PIP3). Activated PIP3 binds to and in turn phosphorylates the enzyme PDK-1, the main activator of AKT, through its pleckstrin homology domain. Activated PDK-1 is responsible for a phosphorylation event at Thr308 of AKT, which induces a conformational change that facilitates further phosphorylation of AKT at Ser 473 by PDK-2.

PDK-1 phosphorylation of downstream kinases is not unique to AKT, as it has been reported to activate p70 S6 kinase and protein kinase C.

The activation of AKT influences multiple events within the cell including the inhibition of apoptosis, the progression of the cell cycle, cellular survival, metabolism, angiogenesis and hormone resistance.

Presently, three family members/isoforms of AKT have been identified: AKT 1, AKT 2 and AKT 3 (also known as PKBα, PKBβ and PKBγ). The family members share 80% amino acid sequence homology and all retain similar regional structure. They possess an N-terminal pleckstrin homology (PH) domain, a catalytic domain, a short α helical linker region and a carboxyl terminal domain. The PH domain permits binding of proteins to the cell membrane through a phospholipid interaction. The catalytic domain of AKT family members contains two residues essential for kinase activation, namely Thr308 and Ser 473. In turn AKT can phosphorylate any protein containing the RXRXXS/T-B motif where X represents any amino acid and B represents bulky hydrophobic residues.

Turning to the cellular function of AKT, hyperactivation of AKT has been linked to the inhibition of cellular apoptosis due to phosphorylation and negative regulation of the forkhead family of transcription factors which regulate various genes responsible for instigating death processes including FKHR, FKHRL1 and AFX. Conversely, AKT has been reported to upregulate genes which are known to be anti-apoptotic including IKK and CREB. It is this mixture of positive and negative regulation which highlights the importance of AKT in regulating apoptosis. AKT promotes unwanted cell survival through its phosphorylation of several key apoptotic proteins including Bad and Pro-caspase 9, thus rendering them inactive and preventing signalling through this pathway. AKT activates and inhibits multiple mechanisms which have a major role in the progression of the cell cycle, ultimately leading to cell proliferation. The well characterised cell cycle regulator and tumour suppressor protein p53 can be dysregulated via AKT phosphorylation and activation of the main p53 negative regulator MDM2. Phosphorylated MDM2 translocates to the nucleus where it prevents p53 transcription. The inhibition of p53 allows aberrant proliferation of the cell and progression towards a benign state.

In a similar fashion, AKT can also phosphorylate p27kip1 and p21; two main inhibitors of cell cycle progression, leading to loss of function, resulting in unchecked cell cycle progress and excessive proliferation.

AKT activation causes an increase in the rate of glycolysis by increasing the rate of glucose metabolism. It has also been reported that activated AKT stimulates the transport of amino acids and supports mTOR dependent increases in protein translation. Proangiogenic factors, such as vascular endothelial growth factor (VEGF), have been reported to activate AKT, ultimately resulting in inhibition of endothelial cell apoptosis, as well as activating endothelial nitric oxide synthase (eNOS). The sum result of this is rapid neovascularisation and cell migration.

Hypoxia driven angiogenesis, primarily mediated by hypoxia inducible factor (HIF 1α), can lead to the induction of multiple proteins including VEGF. Increased activated AKT has been reported to increase HIF-1α expression leading to an increase in angiogenesis independent of a hypoxic environment. Recent data has shown that HIF-1α activity in invasive breast cancer is correlated with increased activated AKT1 phosphorylation.

Estrogen receptor (ER) and androgen receptor (AR) inhibitors designed to inhibit cell signalling and induce apoptosis, are vital tools in cancer therapies. Incidence of resistance to these drugs arises rapidly in cancers including prostate, breast and ovarian. AKT has been reported to phosphorylate androgen receptors, leading to inhibition of AR activity and blockade of normal apoptotic signalling in prostate cancer induced by androgens.

In a similar manner, activation of AKT leads to phosphorylation of ERα resulting in an inhibition of tamoxifen-mediated apoptosis or tumour regression, coupled with the creation of an estrogen independent signalling pathway. Activated AKT2 has been identified as a promoter of ERα transcription in the presence or absence of estrogen increasing the rate of proliferation of breast cancer cells.

Hyperactivated AKT has been reported in a range of cancers compared to normal tissues including breast, lung, prostate, gastric, ovary, pancreas, thyroid, glioblastoma and haemological cancers. Phosphorylation of AKT has also been associated with clinical characteristics including increased stage and grade of tumour and poor prognosis. The activation of AKT can arise from a number of different genetic mutations in the AKT/PI-3K pathway.

Somatic mutations in the PI-3KCA gene have been widely reported in a large variety of tumours including breast, prostate and head and neck. A large number of these mutations will increase the copy number of the gene leading to an increase in PI-3K activity. A recent study has identified a PI-3K mutation which selectively phosphorylates AKT in colon cancer which results in increased cell proliferation and invasion.

Any mutation which increases the activity of the PI-3K pathway will ultimately result in an increased activation of AKT. Gene amplifications are common occurrences in cancer. Amplifications of AKT2 have been reported in ovarian, pancreatic, breast and head and neck squamous cell carcinoma. No amplifications or mutations in AKT3 have been reported to date although deletion mutations leading to hyperactivation and amplification mutations have been reported associated with AKT1. One mutation, E17K, results in pathological localization of AKT1 to the cell membrane, inducing its activation and resultant downstream signalling and cellular transformation. In vivo, this mutation has been shown to induce leukaemia in mice.

Phosphatase and tensin homolog deleted on chromosome 10 (PTEN) is a tumour suppressor gene known to negatively regulate AKT function. In cancer, loss of PTEN function results in constitutive phosphorylation of AKT and other downstream effectors of the PI-3K pathway. Loss of PTEN, due to deletion mutations or promoter methylation, has been reported in a number of different cancers including glioblastoma, endometrial, lung, breast, prostate and thyroid. This loss is commonly associated with hyperactivation of AKT. Recent studies have shown that loss of heterozygosity (LOH) at the PTEN gene was directly correlated to increased AKT activation and chemoresistance in gastric carcinomas and decreased progesterone receptor expression in breast carcinomas.

AKT activation is commonly initiated at the cell surface through a signalling event at a receptor, usually one of the tyrosine kinase family. Two tyrosine kinase receptors commonly amplified or overexpressed in cancer are HER2 and EGFR. In HER2 overexpressing tumours, there is often a hyperactivation of AKT, which has been reported in ovarian, stomach and bladder cancer. Similarly, in EGFR overexpressing tumours, particularly those with the EGFRvIII activating mutation, selective activation of AKT has been reported in a range of cancers including non-small cell lung cancers, breast, ovarian and most commonly high grade gliomas.

Examples of AKT inhibitors are provided in WO 2008/070134, WO 2008/070016 and WO 2008/070041. These documents provide specific naphthyridine compounds fused to a five membered heterocycle. Further examples of AKT inhibitors are provided in WO2011/055115.

SUMMARY OF THE INVENTION

In a first aspect the present invention provides a compound according to Formula (I):

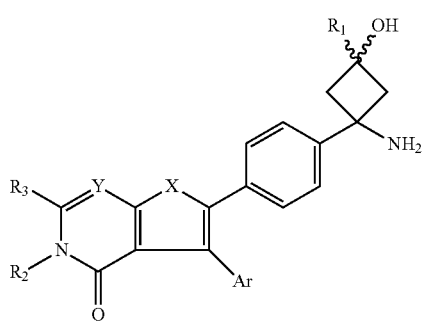

wherein:
Y is selected from N, and CR, where R is hydrogen, Z, cyano, or CONR'R" where R' and R" are independently H or Z;
X is O, NR'" or S where R" is hydrogen or Z;
Ar is aryl or heteroaryl;
$R^1$ is hydrogen or Z;
$R^2$ is Z;
$R^3$ is hydrogen, Z, or $NR^4R^5$ where $R^4$ and $R^5$ are independently H or Z;
wherein Z refers to an aliphatic group containing at least carbon and hydrogen and containing 1 to 6 carbon atoms; wherein Z may be straight chained or branched; may contain no ring structures or may contain one or more rings; wherein Z may be saturated or unsaturated; wherein Z may be unsubstituted or substituted with one or more heteroatoms such as CN, $CO_2H$, $CONH_2$, CONHR, $CONR^aR^b$, $CO_2R$, $NH_2$, NHR, $NR^aR^b$, OH, OR, SH, SR, F, Cl, Br and I, wherein each R, $R^a$ and $R^b$ are independently selected groups attached to the atom to which the group joins through a carbon atom of each group, including wherein $R^a$ and $R^b$ form a heterocycle that includes the heteroatom to which they are attached; wherein if more than one heteroatom substituent is present, the substituents are independently selected from one another unless they form a part of a particular functional group; wherein any heteroatom substituents may in turn be substituted with further carbon-containing groups;
wherein "aryl" refers to a group containing at least one ring that is aromatic; wherein each one or more rings of said aryl group may be individually selected to contain only carbon atoms, alternatively wherein each one or more rings of said aryl group may contain both carbon atoms and from 1 to 4 heteroatoms selected from O, N and S; wherein said heteroatoms may be substituted;
and pharmaceutically acceptable salts, stereoisomers and tautomers thereof.

In preferred embodiments X is O or S. In particularly preferred embodiments X is O. In other particularly preferred embodiments X is S or N—$CH_3$.

In preferred embodiments Y is nitrogen.

In preferred embodiments $R^3$ is hydrogen.

In preferred embodiments $R^2$ is halo substituted Z, more preferably fluoro substituted Z. In particularly preferred embodiments $R^2$ is 2,2,2 trifluoroethyl.

Where Ar is heteroaryl it is preferably a nitrogen-containing heteroaryl moiety.

In preferred embodiments, Ar is phenyl, 2-pyridyl, 3-pyridyl, 4-pyridyl or thiophene. In particularly preferred embodiments Ar is phenyl.

In preferred embodiments $R^1$ is methyl.

In preferred embodiments the hydroxyl group bound to the cyclobutane moiety of the compounds of the invention is trans with respect to the amine group also bound to the cyclobutane moiety. Without wishing to be bound by theory, this trans arrangement appears generally to increase biochemical and cellular potency and therefore confers on these compounds advantageous properties.

In other preferred embodiments the hydroxyl group bound to the cyclobutane moiety of the compounds of the invention is cis with respect to the amine group also bound to the cyclobutane moiety. Again, without wishing to be bound by theory, this cis arrangement confers on these compounds advantageous properties over those known in the art.

Other preferred embodiments of the compounds according to the invention appear throughout the specification and in particular in the examples.

In a second aspect the present invention provides a pharmaceutical composition comprising a pharmaceutical carrier and, dispersed therein, a compound of the invention as herein described.

In a third aspect the present invention provides the compounds of the invention as herein described for use in therapy.

In a fourth aspect the present invention provides the compounds of the invention as herein described for use in the treatment or prevention of cancer.

In a fifth aspect the present invention provides a method of treating cancer in a patient in need thereof comprising administering one or more of the compounds of the invention as herein described.

DETAILED DESCRIPTION OF THE INVENTION

The term Z refers to an aliphatic group containing at least carbon and hydrogen and containing 1 to 6 carbon atoms; wherein Z may be straight chained or branched; wherein Z may contain no ring structures or may contain one or more rings; wherein Z may be saturated or unsaturated; wherein Z may be unsubstituted or substituted with one or more heteroatoms; wherein if more than one hetero-substituent is present, the substituents are independently selected from one another unless they form a part of a particular functional group; wherein any heteroatom substituents may in turn be substituted with further carbon-containing groups. In one aspect of the invention, Z is Z' as defined herein below.

"Alkyl" refers to an aliphatic group containing at least carbon and hydrogen and containing 1 to 15 carbon atoms, such as 1 to 10 carbon atoms. Attachment to the alkyl group occurs through a carbon atom.

A "$C_n$ alkyl" group refers to an aliphatic group containing n carbon atoms. For example, a $C_1$-$C_{10}$ alkyl group contains 1, 2, 3, 4, 5, 6, 7, 8, 9 or 10 carbon atoms.

The term "lower alkyl" refers to an aliphatic group containing at least carbon and hydrogen and containing 1 to 6 carbon atoms An alkyl group may be straight chained or it may be branched.

An alkyl group may contain no ring structures or it may contain one or more rings.

For example, a "cycloalkyl" group contains at least one ring. It is understood that attachment to a cycloalkyl group is via a ring of the cycloalkyl group. Each ring may contain 3 to 10 atoms, such as 4 to 8 or 5 to 7 atoms. Each ring may be independently selected to contain just carbon atoms or to contain both carbon atoms and from 1 to 4 heteroatoms selected from O, N and S. For cyclo-heteroalkyl groups (i.e. cycloalkyl groups that contain one or more heteroatoms), attachment to the cycloalkyl group may occur either through a carbon atom or, if one or more heteroatoms are contained in a ring, attachment may also occur through a heteroatom contained in a ring.

For example, a cycloalkyl group may be mono-cyclic or bi-cyclic.

Thus, a "$C_n$ cycloalkyl" group contains n carbon atoms. All n carbon atoms may be contained in the ring(s) of the cycloalkyl group or one or more of the carbons may not be contained in the ring(s) and may instead form one or more chains branching from the ring.

If a $C_n$ alkyl group is joined to a separate $C_m$ alkyl group containing m carbon atoms to form, for example, a heterocycle, the two alkyl groups contain a total number of m+n carbon atoms.

An alkyl group may be saturated or unsaturated. Thus, the alkyl group may be an alkenyl group (i.e. contain a carbon-carbon double bond) and/or an alkynyl group (i.e. contain a carbon-carbon triple bond). If the alkyl group is unsaturated, it may contain at least 2 carbon atoms. It is understood that any unsaturated portions of an alkyl group are non-aromatic (aromatic groups fall within the scope of the definition of "aryl"). Any part of the alkyl group may be unsaturated, for example the straight, branched or cyclic portion of an alkyl group may contain a carbon-carbon double bond or a carbon-carbon triple bond. Attachment to an unsaturated alkyl group may occur through the unsaturated part of the alkyl group or may occur through the unsaturated part of the group.

For example, an unsaturated alkyl group may contain 1 to 4 carbon-carbon double bonds or 1 to 3 carbon-carbon triple bonds or 1 to 4 of a combination of carbon-carbon double bonds and carbon-carbon triple bonds.

An alkyl group may be substituted with one or more heteroatoms or it may be unsubstituted (i.e. not contain any heteroatoms). If more than one hetero-substituent is present, the substituents are independently selected from one another unless they form a part of a particular functional group (e.g. an amide group).

The heteroatom substituents may in turn be substituted with further carbon-containing groups. In this case, the $C_n$ or $C_m$ prefix that defines the substituted alkyl group refers to the total number of carbons contained in the group, i.e. including the carbon atoms contained in any substituted heteroatomic groups, and the total alkyl group contains 1 to 15 carbon atoms as defined previously.

Accordingly, if the alkyl group is substituted, it may, for example, contain one or more of CN, $CO_2H$, $CONH_2$, CONHR, $CONR^aR^b$, $CO_2R$, $NH_2$, NHR, $NR^aR^b$, OH, OR, SH, SR, F, Cl, Br and I, wherein each R, $R^a$ and $R^b$ are independently selected groups (e.g. alkyl/aryl groups) attached to the atom to which the group joins through a carbon atom of each group, including wherein $R^a$ and $R^b$ form a heterocycle that includes the heteroatom to which they are attached. A group containing two $C_m$-$C_n$ alkyl moieties that form a cycle that includes, for example, the heteroatom to which they are attached may contain from $C_{2m}$ to $C_{2n}$ carbon atoms.

Examples of unsubstituted saturated alkyl groups containing no cyclic structures include methyl, ethyl, n-propyl, sec-propyl, n-butyl, sec-butyl, tert-butyl, pentyl (branched or unbranched), hexyl (branched or unbranched), heptyl (branched or unbranched), octyl (branched or unbranched), nonyl (branched or unbranched), and decyl (branched or unbranched).

Examples of unsubstituted saturated cyclic alkyl groups include cyclopropyl, cyclobutyl, cyclopentyl and cyclohexyl.

Examples of unsaturated alkyl groups include ethenyl, propenyl, butenyl, 2-methybutenyl and cyclohexenyl.

Although not in strict conformity with the IUPAC definition, it will be appreciated that the foregoing may loosely be referred to as "alkyl".

It will also be appreciated that, although not in strict conformity with IUPAC, the term "aryl" may be understood to include "heteroaryl".

According to these definitions of alkyl and aryl, the present invention also provides compounds according to Formula (I):

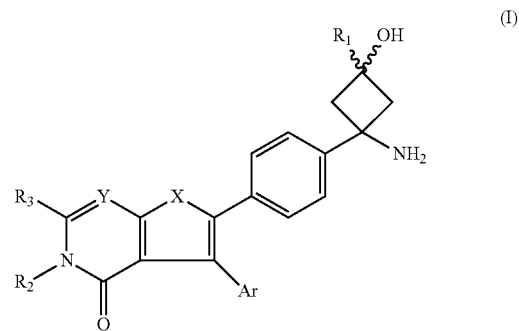

wherein:

Y is selected from N, and CR, where R is hydrogen, lower alkyl, cyano, or CONR'R" where R' and R" are independently H or lower alkyl;

X is O, NR'" or S where R" is hydrogen or lower alkyl;

Ar is aryl;

$R^1$ is hydrogen or lower alkyl;

$R^2$ is lower alkyl;

$R^3$ is hydrogen, lower alkyl, or $NR^4R^5$ where $R^4$ and $R^5$ are independently H or lower alkyl;

and pharmaceutically acceptable salts, stereoisomers and tautomers thereof.

In one aspect of the invention, Z is preferably Z'. Z' refers to a lower alkyl, lower heteroalkyl, lower cycloalkyl, lower cycloheteroalkyl, lower alkenyl, lower alkynyl, lower heteroalkenyl, lower heteroalkynyl, lower cycloalkenyl or lower cyclo-heteroalkenyl group.

In reference to Z', "alkyl group" (alone or in combination with another term(s)) means a straight- or branched-chain saturated hydrocarbyl substituent typically containing 1 to 15 carbon atoms, such as 1 to 10, 1 to 8, 1 to 6, or 1 to 4 carbon atoms. Attachment to the alkyl group occurs through a carbon atom. Examples of such alkyl group substituents include methyl, ethyl, n-propyl, isopropyl, n-butyl, isobutyl, sec-butyl, tert-butyl, pentyl (branched or unbranched), hexyl (branched or unbranched), heptyl (branched or unbranched), octyl (branched or unbranched), nonyl (branched or unbranched), and decyl (branched or unbranched).

In reference to Z', "alkenyl group" (alone or in combination with another term(s)) means a straight- or branched-chain hydrocarbyl substituent containing one or more double bonds and typically 2 to 15 carbon atoms; such as 2 to 10, 2 to 8, 2 to 6 or 2 to 4 carbon atoms. Attachment to the alkenyl group occurs through a carbon atom. Examples of such substituents include ethenyl (vinyl), 2-propenyl, 3-propenyl, 1,4-pentadienyl, 1,4-butadienyl, 1-butenyl, 2-butenyl, 3-butenyl, pentenyl and hexenyl.

In reference to Z', "alkynyl group" (alone or in combination with another term(s)) means a straight- or branched-chain hydrocarbyl substituent containing one or more triple bonds and typically 2 to 15 carbon atoms; such as 2 to 10, 2 to 8, 2 to 6 or 2 to 4 carbon atoms. Attachment to the alkynyl group occurs through a carbon atom. Examples of such substituents include ethynyl, 2-propynyl, 3-propynyl, 2-butynyl, and 3-butynyl.

In reference to Z', "cycloalkyl group" (alone or in combination with another term(s)) means a saturated cyclic hydrocarbyl substituent containing 3 to 15 carbon ring atoms. A cycloalkyl may be a single carbon ring, which typically contains 3 to 10 carbon ring atoms and more typically 4 to 8 or 5 to 7 ring atoms. It is understood that attachment to a cycloalkyl group is via a ring atom of the cycloalkyl group. Examples of single-ring cycloalkyls include cyclopropyl, cyclobutyl, cyclopentyl, and cyclohexyl. A cycloalkyl may alternatively be polycyclic or contain more than one ring. Examples of polycyclic cycloalkyls include bridged, fused, and spirocyclic structures.

In reference to Z', "cycloalkenyl group" (alone or in combination with another term(s)) means a cyclic hydrocarbyl substituent containing one or more double bonds and typically containing 3 to 15 carbon ring atoms. A cycloalkenyl may be a single carbon ring, which typically contains 3 to 10 carbon ring atoms and more typically 4 to 8 or 5 to 7 ring atoms. It is understood that attachment to a cycloalkenyl group is via a ring atom of the cycloalkenyl group. A cycloalkenyl may alternatively be polycyclic or contain more than one ring.

In reference to Z', "heteroalkyl group" (alone or in combination with another term(s)) means an alkyl group containing 1 to 15 carbon atoms, such as 1 to 10, 1 to 8, 1 to 6, or 1 to 4 carbon atoms in which one or more carbon atoms is substituted with a heteroatom.

In reference to Z', "heteroalkenyl group" (alone or in combination with another term(s)) means an alkenyl group containing 2 to 15 carbon atoms, such as 1 to 10, 1 to 8, 1 to 6, or 1 to 4 carbon atoms in which one or more carbon atoms is substituted with a heteroatom.

In reference to Z', "heteroalkynyl group" (alone or in combination with another term(s)) means an alkynyl group containing 2 to 15 carbon atoms, such as 2 to 10, 2 to 8, 2 to 6, or 2 to 4 carbon atoms in which one or more carbon atoms is substituted with a heteroatom.

In reference to Z', "cycloheteroalkyl group" (alone or in combination with another term(s)) means a cycloalkyl group containing 3 to 15 carbon ring atoms in which one or more carbon atoms is substituted with a heteroatom.

In reference to Z', "cycloheteroalkenyl group" (alone or in combination with another term(s)) means a cycloalkenyl group containing 3 to 15 carbon ring atoms in which one or more carbon atoms is substituted with a heteroatom.

In reference to Z', if more than one heteroatom is present in a heteroalkyl, heteroalkenyl, heteroalkynyl, cycloheteroalkyl or cycloheteroalkenyl group, each heteroatom is independently selected from one another unless they form part of a particular functional group (e.g. an amide group).

In reference to Z', for cycloheteroalkyl and cycloheteroalkenyl groups attachment to the cycloheteroalkyl or cycloheteroalkenyl group may occur either through a carbon atom or, if one or more heteroatoms are contained in a ring, attachment may also occur through a heteroatom contained in a ring.

In reference to Z', the heteroatom substituents in a heteroalkyl, heteroalkenyl, heteroalkynyl, cycloheteroalkyl or cycloheteroalkenyl group may in turn be substituted with further carbon-containing groups. In this case, the $C_n$ or $C_m$ prefix that defines the substituted heteroalkyl, heteroalkenyl, heteroalkynyl, cycloheteroalkyl or cycloheteroalkenyl group refers to the total number of carbons contained in the group, i.e. including the carbon atoms contained in any substituted heteroatomic groups, and the total heteroalkyl, heteroalkenyl, heteroalkynyl, cycloheteroalkyl or cycloheteroalkenyl group contains 1 or 2 to 15 carbon atoms as defined previously.

In reference to Z', the terms "lower alkyl" "lower heteroalkyl", "lower heteroalkenyl", "lower heteroalkynyl", "lower cycloheteroalkyl" and "lower cycloheteroalkenyl" refer to a substituent having the respective above definition containing 1 to 6 carbon atoms.

In reference to Z', a "$C_n$" group refers to a group containing n carbon atoms. For example, a $C_1$-$C_{10}$ group contains 1, 2, 3, 4, 5, 6, 7, 8, 9 or 10 carbon atoms.

In reference to Z', if a $C_n$ group is joined to a separate $C_m$ group containing m carbon atoms to form, for example, a heterocycle, the two groups contain a total number of m+n carbon atoms.

In reference to Z', a "$C_n$" cycloalkyl or cycloalkenyl group contains n carbon atoms. All n carbon atoms may be contained in the ring(s) of the cycloalkyl or cycloalkenyl group or alternatively one or more of the carbons may not be contained in the ring(s) and may instead form one or more chains branching from the ring.

The term "aryl group" refers to a group containing at least one ring that is aromatic, wherein each aromatic ring contains only carbon atoms.

The term "heteroaryl group" refers to a group containing at least one ring that is aromatic, wherein at least one aromatic ring contains both carbon atoms and from 1 to 4 heteroatoms selected from O, N and S. For heteroaryl groups containing more than one aromatic ring, each ring is independently selected to contain only carbon atoms or to contain both carbon atoms and from 1 to 4 heteroatoms selected from O, N and S, provided at least one ring contains both carbon atoms and from 1 to 4 heteroatoms selected from O, N and S.

It is noted that the heteroatoms contained in a ring of a heteroaryl group may be substituted, for example forming an N-oxide.

Where an aryl group is stated as being substituted at a particular position, attachment of the position to the aryl group is onto the aromatic ring of the aryl group itself rather than the position being joined to the aryl group through any non-aromatic side-chain of the aryl group. For example, when $R^1$ is an aryl group in $CR^1$, the C is attached to the aromatic part of the aryl group.

For heteroaryl groups, attachment to the heteroaryl group may occur either through a carbon atom or attachment may also occur through a heteroatom contained in a ring.

The aromatic group of an aryl group or a heteroaryl group may be mono-cyclic or bi-cyclic, wherein one or both of the rings of a bi-cyclic system is aromatic.

Examples of aryl and heteroaryl groups include acridinyl, phenyl, carbazolyl, cinnolinyl, quinoxalinyl, pyrazolyl, benzotriazolyl, furanyl, naphthyl, thienyl, thiazolyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetrahydroquinoline, benzimidazolyl and melaminyl.

It is noted that the term "heterocycle" includes within its scope both cyclic aliphatic groups containing one or more heteroatoms within the ring system and heteroaryl groups containing one or more heteroatoms within the ring system.

The term "halo" refers to a group selected from chlorine, fluorine, bromine and iodine.

The present invention will now be further described. In the following passages different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

In whatever aspect, the compounds of the present invention may possess some aspect of stereochemistry. For example, the compounds may possess chiral centres and/or planes and/or axes. As such, the compounds may be provided as single stereoisomers, single diastereomers, mixtures of stereoisomers or as racemic mixtures. Stereoisomers are known in the art to be molecules that have the same molecular formula and sequence of bonded atoms, but which differ in their spatial orientations of their atoms and/or groups.

In addition, the compounds of the present invention may possess tautomerism. Each tautomeric form is intended to fall within the scope of the invention.

In addition, the compounds of the present invention may be provided as a pro-drug. Pro-drugs are transformed, generally in vivo, from one form to the active forms of the drugs described herein. For example, a prodrug may be formed by protecting the amine appending the cyclobutane as a physiological hydrolyzable amide. Alternatively or additionally, another nitrogen atom within the molecule may be protected as a physiological hydrolyzable amide.

In addition, the compounds of the present invention may be provided in the form of their pharmaceutically acceptable salts or as co-crystals. For example, the compounds may be provided having protonated amine groups.

The term "pharmaceutically acceptable salt" refers to ionic compounds formed by the addition of an acid to a base. The term refers to such salts that are considered in the art as being suitable for use in contact with a patient, for example in vivo and pharmaceutically acceptable salts are generally chosen for their non-toxic, non-irritant characteristics.

The term "co-crystal" refers to a multi-component molecular crystal, which may comprise non-ionic interactions.

Pharmaceutically acceptable salts and co-crystals may be prepared by ion exchange chromatography or by reacting the free base or acidic form of a compound with stoichiometric amounts or with an excess of the desired salt-forming inorganic or organic acid or base in one or more suitable solvents.

Salts known in the art to be generally suitable for use in contact with a patient include salts derived from inorganic and/or organic acids, including the hydrobromide, hydrochloride, sulphate, bisulphate, nitrate, acetate, oxalate, oleate, palmitate, stearate, laurate, benzoate, lactate, phosphate, tosylate, citrate, maleate, fumarate, succinate and tartrate. These may include cations based on the alkali and alkaline earth metals, such as sodium, potassium, calcium and magnesium, as well as ammonium, tetramethylammonium, tetraethylammonium. Further reference is made to the number of literature sources that survey suitable pharmaceutically acceptable salts, for example the Handbook of pharmaceutical salts published by IUPAC.

In addition, the compounds of the present invention may sometimes exist as zwitterions, which are considered as part of the invention.

The compounds of the present invention are useful in the treatment of medical conditions associated with disordered cell growth, including, but not restricted to, cancer, in particular cancers associated with overactivity of AKT occurring either from a direct change within the kinase itself such as may occur following a mutation within any of its subunits or from increased upstream activity including but not restricted to increased PI3K or PDK activity. Increased PI3K activity may have occurred through loss of the tumor suppressor PTEN.

For example, cancers include cardiac cancers, lung cancers, gastrointestinal cancers, genitourinary tract cancers, liver cancers, bone cancers, nervous system cancers, gynecological cancers, hematologic cancers, skin cancers and adrenal gland cancers.

For example, cancers include adrenal tumors, bile duct, bladder, blood, bone and connective tissue, brain and central nervous system, breast, cervical, colon and rectal (colorectal), endometrial, esophageal, gallbladder, head and neck, Hodgkin's Lymphoma, hypopharangeal, kidney, laryngeal, leukemias, liver, lung, lymphoma, mediastinal tumors, melanoma (malignant melanoma), mesothelioma, multiple myeloma, nasal cavity, nasopharyngeal, neuroendocrine tumors, non-Hodgkin's lymphoma, oral, oesophagus, oropharyngeal, ovarian, pancreas, paranasal sinus, parathyroid, penis, pituitary tumors, prostate, salivary gland, sarcoma, skin, spine, stomach, testicular, thyroid, urethra, uterine, vaginal and vulvar.

The compounds of the present invention are also useful in preparing a medicament that is useful in treating the diseases described above, in particular cancer.

The compounds of the present invention may selectively inhibit one or two of the AKT protein family over the other AKT isoform(s). For example, the compounds may selectively inhibit one or two of AKT1, AKT2 or AKT3 over the other isoform(s) of AKT.

For example, the compounds of the present invention may inhibit at least AKT1 and/or AKT2. For example, the compounds may selectively inhibit AKT1 and/or AKT2 over AKT3. Moreover, certain compounds may selectively inhibit AKT2 over AKT1 and AKT3

The present invention is further directed to a method of inhibiting AKT activity which comprises administering to a mammal in need thereof a pharmaceutically effective amount of the compound of the present invention.

The compounds of this invention may be administered to mammals, including humans, either alone or, in combination with pharmaceutically acceptable carriers, excipients or diluents, in a pharmaceutical composition, according to standard pharmaceutical practice. The compounds can be administered orally or parenterally, including the intravenous, intramuscular, intraperitoneal, subcutaneous, rectal and topical routes of administration.

The present invention also includes within its scope the use of the compounds of the present invention in combination with a second drug in the treatment of cancer. The second drug may be a drug that is already known in the art in the treatment of cancer.

In particular, cancers often become resistant to therapy. The development of resistance may be delayed or overcome by the administration of a combination of drugs that includes the compounds of the present invention.

For example, drugs that may be used in combination with the compounds of the present invention may target the same or a similar biological pathway to that targeted by the compounds of the present invention or may act on a different or unrelated pathway.

Depending on the disease to be treated, a variety of combination partners may be coadministered with the compounds of the present invention. The second active ingredient may include, but is not restricted to: alkylating agents, including cyclophosphamide, ifosfamide, thiotepa, melphalan, chloroethylnitrosourea and bendamustine; platinum derivatives, including cisplatin, oxaliplatin, carboplatin and satraplatin; antimitotic agents, including vinca alkaloids (vincristine, vinorelbine and vinblastine), taxanes (paclitaxel, docetaxel), epothilones and inhibitors of mitotic kinases including aurora and polo kinases; topoisomerase inhibitors, including anthracyclines, epipodophyllotoxins, camptothecin and analogues of camptothecin; antimetabolites, including 5-fluorouracil, capecitabine, cytarabine, gemcitabine, 6-mercaptopurine, 6-thioguanine, fludarabine, methotrexate and premetrexed; protein kinase inhibitors, including imatinib, gefitinib, sorafenib, sunitinib, erlotinib, dasatinib, and lapatinib; proteosome inhibitors, including bortezomib; histone deacetylase inhibitors, including valproate and SAHA; antiangiogenic drugs, including bevacizumab; monoclonal antibodies, including trastuzumab, rituximab, alemtuzumab, tositumomab, cetuximab, panitumumab; conjugates of myoclonal antibodies, including Gemtuzumab ozogamicin, Ibritumomab tiuxetan; hormonal therapies, including antiestrogens (tamoxifen, raloxifen, anastrazole, letrozole, examestane) antiandrogens (Flutamide, Biclutamide) and Luteinisng Hormone Analogues or antagonists.

With regard to combination therapy the compounds of the present invention may be administered separately, sequentially, simultaneously, concurrently or may be chronologically staggered with one or more standard therapeutics such as any of those mentioned above.

The present invention also provides a pharmaceutical composition suitable for clinical use.

In particular, a pharmaceutical composition may comprise a pharmaceutical carrier and, dispersed therein, a therapeutically effective amount of the compounds of the invention. The composition may be solid or liquid. The pharmaceutical carrier is generally chosen based on the type of administration being used and the pharmaceutical carrier may for example be solid or liquid. The compounds of the invention may be in the same phase or in a different phase than the pharmaceutical carrier.

Pharmaceutical compositions may be formulated according to their particular use and purpose by mixing, for example, excipient, binding agent, lubricant, disintegrating agent, coating material, emulsifier, suspending agent, solvent, stabilizer, absorption enhancer and/or ointment base. The composition may be suitable for oral, injectable, rectal or topical administration.

For example, the pharmaceutical composition may be administered orally, such as in the form of tablets, coated tablets, hard or soft gelatine capsules, solutions, emulsions, or suspensions. Administration can also be carried out rectally, for example using suppositories, locally or percutaneously, for example using ointments, creams, gels or solution, or parenterally, for example using injectable solutions.

For the preparation of tablets, coated tablets or hard gelatine capsules, the compounds of the present invention may be admixed with pharmaceutically inert, inorganic or organic excipients. Examples of suitable excipients include lactose, mize starch or derivatives thereof, talc or stearic acid or salts thereof. Suitable excipients for use with soft gelatine capsules include, for example, vegetable oils, waxes, fats and semi-solid or liquid polyols.

For the preparation of solutions and syrups, excipients include, for example, water, polyols, saccharose, invert sugar and glucose.

For injectable solutions, excipients include, for example, water, alcohols, polyols, glycerine and vegetable oil.

For suppositories and for local and percutaneous application, excipients include, for example, natural or hardened oils, waxes, fats and semi-solid or liquid polyols.

The pharmaceutical compositions may also contain preserving agents, solublizing agents, stabilizing agents, wetting agents, emulsifiers, sweeteners, colorants, odorants, buffers, coating agents and/or antioxidants.

For combination therapies, the second drug may be provided in pharmaceutical composition with the present invention or may be provided separately.

Thus, a pharmaceutical formulation for oral administration may, for example, be granule, tablet, sugar-coated tablet, capsule, pill, suspension or emulsion. For parenteral injection for, for example, intravenous, intramuscular or subcutaneous use, a sterile aqueous solution may be provided that may contain other substances including, for example, salts and/or glucose to make to solution isotonic. The anti-cancer agent may also be administered in the form of a suppository or pessary, or may be applied topically in the form of a lotion, solution, cream, ointment or dusting powder.

The present invention also relates to methods of treating or preventing cancer comprising administering a compound according to the present invention as described herein to a subject in need thereof.

EXAMPLES

The present invention will now be described in relation to several examples.

Examples 1 to 20 were synthesised according to the methods described subsequently. Their $IC_{50}$ values versus the AKT1, 2 and 3 isoforms were then determined as described below and are represented in the table at the end of this section, in which the compound numbers correspond to the numbers in the examples.

In addition, the activity of compounds to inhibit pAKT was investigated. Representative examples (eg. 1, 2, 3, 4, 5, 6 and 7) show inhibition of pAKT in PC3 cell lines with an $IC_{50} \leq 500$ nM.

SelectScreen® data was determined at Invitrogen. Plasma protein binding and pharmacokinetic analyses were determined using standard protocols.

Abbreviations

DCM: Dichloromethane; DME: Dimethoxyethane; DMF: N,N-Dimethylformamide; EtOAc: Ethyl acetate; h: Hour: HCl: Hydrochloric acid; HPLC: High Pressure Liquid Chromatography; M: Molar; MeOH: Methanol; NBS: N-Bromosuccinimide; NMR: Nuclear Magnetic Resonance; Min: Minutes; RT: Room temperature; SCX: strong cation exchange; TFA: Trifluoroacetic acid; THF: Tetrahydrofuran.

General Experimental Conditions $^1$H NMR spectra were recorded at ambient temperature using a Bruker Avance (500 MHz) spectrometer with a 5 mm QNP probe. Chemical shifts are expressed in ppm relative to tetramethylsilane.

High Pressure Liquid Chromatography—Mass Spectrometry (LCMS) experiments to determine retention times ($R_T$) and associated mass ions were performed using the following method.

The system consists of an Agilent Technologies 6140 single quadrupole mass spectrometer linked to an Agilent Technologies 1290 Infinity LC system with UV diode array detector and autosampler. The spectrometer has a multimode ionization source (electrospray and atmospheric pressure chemical ionizations) operating in positive and negative ion mode. An LCMS experiment is performed on each sample submitted using the following conditions: LC Column—Zorbax Eclipse Plus C18 RRHD 1.8 micron 50×2.1 mm maintained at 40° C. Mobile phase—A) Water 0.1% Formic Acid B) Acetonitrile 0.1% Formic Acid.

| Gradient - Time | Flow mL/min | % A | % B |
| --- | --- | --- | --- |
| 0.00 | 1.0 | 95 | 5 |
| 1.80 | 1.0 | 0 | 100 |
| 2.20 | 1.0 | 0 | 100 |
| 2.21 | 1.0 | 95 | 5 |
| 2.50 | 1.0 | 95 | 5 |

Detection—MS, UV

MS ionisation method—Multimode (positive and negative ion)

Total experiment time—2.50 mins (approx)

Microwave experiments were carried out using CEM Discover™/Explorer24™ or Biotage Initator™ instruments. Temperatures from 60-300° C. can be achieved, and pressures of up to 20 bar can be reached.

Phase separation was performed using Biotage Isolute® SPE columns.

Unless otherwise indicated, the nomenclature of structures was using "structure=name" from ChemBioDraw Ultra 12.0 (CambridgeSoft).

Unless otherwise indicated, starting materials and intermediates were obtained from commercial suppliers, prepared according to literature procedures (for example WO 2008/070016, WO 2009/148887 and WO 2009/148916) or by standard transformations obvious to one skilled in the art.

Example 1

6-(4-((1s,3s)-1-Amino-3-hydroxy-3-methylcyclobutyl)phenyl)-5-phenyl-3-(2,2,2-trifluoroethyl)furo[2,3-d]pyrimidin-4(3H)-one.HCl Step 1: 5-Phenyl-3-(2,2,2-trifluoroethyl)furo[2,3-d]pyrimidin-4(3H)-one To a solution of 5-phenylfuro[2,3-d]pyrimidin-4(3H)-one (2 g, 9.42 mmol, prepared as described in WO2006/004658) in DMF (20 ml) was charged cesium carbonate (6.76 g, 20.7 mmol) and 1,1,1-trifluoro-2-iodoethane (1.86 ml, 18.9 mmol). The reaction was heated at 70° C. for 18 h under a nitrogen atmosphere. A further 1 eq. of 1,1,1-trifluoro-2-iodoethane was charged to the reaction mixture. The reaction was heated to 100° C. for 5 h before being cooled to RT, diluted with water and extracted twice with ethyl acetate. The organic extracts were washed with brine (3×50 ml), dried (Na$_2$SO$_4$), filtered and concentrated in vacuo. The resultant residue was purified by silica gel chromatography (SiO$_2$, 0 to 50% EtOAc in cyclohexane) affording the title compound as a beige solid (730 mg, 26%). LCMS $R_T$=1.27 min, M+H$^+$=295.

Step 2: 6-Bromo-5-phenyl-3-(2,2,2-trifluoroethyl)furo[2,3-d]pyrimidin-4(3H)-one

To a solution of 5-phenyl-3-(2,2,2-trifluoroethyl)furo[2,3-d]pyrimidin-4(3H)-one (730 mg, 2.48 mmol) in DMF (10 ml) at 0° C. was added bromine (0.153 ml, 2.98 mmol). The reaction mixture was stirred at 0° C. for 1 h and then 3 h at RT. The reaction mixture was diluted with EtOAc (50 ml) and 20% w/w aq. sodium thiosulfate solution (50 ml) and the layers were separated. The organic layer was further washed with brine (2×50 ml), dried (Na$_2$SO$_4$) and concentrated in vacuo affording the title compound as an orange solid. LCMS $R_T$=1.40 min, M+H$^+$=373/375.

Step 3: tert-Butyl((1s,3s)-3-hydroxy-3-methyl-1-(4-(4-oxo-5-phenyl-3-(2,2,2-trifluoroethyl)-3,4-dihydrofuro[2,3-d]pyrimidin-6-yl)phenyl)cyclobutyl)carbamate To a solution of tert-butyl((1s,3s)-3-hydroxy-3-methyl-1-(4-(4,4,5,5-tetramethyl-1,3,2-dioxaborolan-2-yl)phenyl)cyclobutyl)carbamate (Intermediate 1, 150 mg, 0.372 mmol, see below for preparation) and 6-bromo-5-phenyl-3-(2,2,2-trifluoroethyl)furo[2,3-d]pyrimidin-4(3H)-one (132 mg, 0.354 mmol) in DME (6 ml) was added a solution of potassium carbonate (245 mg, 1.77 mmol) in water (1.5 ml). The reaction mixture was degassed by bubbling nitrogen through the reaction mixture for 5 min. Tetrakis(triphenylphosphine)palladium(0) (40.9 mg, 0.035 mmol) was then charged to the reaction and the reaction mixture heated at 80° C. overnight under an atmosphere of nitrogen. After allowing to cool to RT, the reaction mixture was concentrated in vacuo and the residue partitioned between water and ethyl acetate. The aqueous phase was extracted once more with ethyl acetate. The combined organic extracts were dried (MgSO$_4$), filtered and concentrated in vacuo. The resultant residue was subjected to flash chromatography (SiO$_2$, gradient 0 to 5% methanol in DCM) to afford the title compound as a brown gum (170 mg, 84%). $^1$H NMR (500 MHz, CDCl$_3$): δ 8.05 (1H, s), 7.55-7.39 (7H, m), 7.31 (2H, d), 4.90 (1H, br s), 4.69-4.64 (2H, m), 4.30 (1H, br s) 2.96 (2H, br s), 2.78 (d, 2H), 1.40 (9H, br s), 1.22 (3H, s).

Step 4: 6-(4-((1s,3s)-1-Amino-3-hydroxy-3-methyl-cyclobutyl)phenyl)-5-phenyl-3-(2,2,2-trifluoroethyl)furo[2,3-d]pyrimidin-4(3H)-one.HCl To a solution of tert-butyl ((1s,3s)-3-hydroxy-3-methyl-1-(4-(4-oxo-5-phenyl-3-(2,2,2-trifluoroethyl)-3,4-dihydrofuro[2,3-d]pyrimidin-6-yl)phenyl)cyclobutyl)carbamate (170 mg, 0.298 mmol) in DCM (4 ml) was charged TFA (2 ml). The reaction was then stirred at RT for 10 min. The solvent was removed in vacuo, the residue neutralised using saturated aq. NaHCO$_3$ and extracted with DCM. The resulting biphasic solution was separated using a phase separator, the solvents were removed in vacuo and the resulting residue was subjected to flash chromatography (SiO$_2$, gradient 0 to 10% methanol in DCM) to afford the product as the free base. The material was dissolved in 1,4-dioxane and a solution of HCl (1.5 eq.) in MeOH added. After stirring for 30 min, the precipitate that formed was collected by filtration and washed with diethyl ether. The material was then freeze dried (CH$_3$CN:H$_2$O) to afford the title compound as a white solid (52 mg, 37%). LCMS R$_T$=0.89 min, M+H$^+$=470. $^1$H NMR (500 MHz, CD$_3$OD): δ 8.41 (1H, s), 7.61 (2H, d), 7.47-7.42 (7H, m), 4.88 (2H, m), 2.81-2.84 (2H, m), 2.62-2.60 (2H, m), 1.22 (3H, s).

Intermediate 1: tert-Butyl((1s,3s)-3-hydroxy-3-methyl-1-(4-(4,4,5,5-tetramethyl-1,3,2-dioxaborolan-2-yl)phenyl)cyclobutyl)carbamate

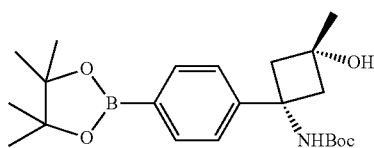 [SMILES: CC(C)(C)OC(=O)N[C@]1(c2ccc(B3OC(C)(C)C(C)(C)O3)cc2)C[C@](C)(O)C1]

Step 1: (1s,3s)-3-Amino-1-methyl-3-(4-(4,4,5,5-tetramethyl-1,3,2-dioxaborolan-2-yl)phenyl)cyclobutanol To a solution of 2-((1s,3s)-3-hydroxy-3-methyl-1-(4-(4,4,5,5-tetramethyl-1,3,2-dioxaborolan-2-yl)phenyl)cyclobutyl)isoindoline-1,3-dione (4.0 g, 9.23 mmol, prepared as described on WO2010/104933) in ethanol (100 ml) was charged hydrazine hydrate (4.53 ml, 92 mmol) at RT. The reaction was then heated at 80° C. for 4 h and stirred overnight at RT. During this time a thick white precipitate formed. Ethanol was added to break up the solid which was collected by filtration through a sintered funnel. The filtrate was concentrated in vacuo to almost dryness, taken up in DCM (100 ml) and washed with water:brine (1:1). The biphasic mixture was separated using a phase separator and the organic layer concentrated in vacuo to afford a yellow oil which solidified on standing. A second batch of material was isolated by extracting the aqueous portion twice with ethyl acetate. The organic layers were combined, dried (MgSO$_4$), filtered and concentrated in vacuo affording the title compound as an off-white solid (1.8 g, 63%). $^1$H NMR (500 MHz, CDCl$_3$): δ 7.79 (2H, d), 7.24 (2H, d), 2.47-2.44 (2H, m), 2.22-2.19 (2H, m), 1.31 (3H, s), 1.34 (12H, s).

Step 2: tert-Butyl((1s,3s)-3-hydroxy-3-methyl-1-(4-(4,4,5,5-tetramethyl-1,3,2-dioxaborolan-2-yl)phenyl)cyclobutyl)carbamate To a solution of (1s,3s)-3-amino-1-methyl-3-(4-(4,4,5,5-tetramethyl-1,3,2-dioxaborolan-2-yl)phenyl)cyclobutanol (1.77 g, 5.84 mmol) in DCM (70 ml) was charged di-tert-butyl dicarbonate (2.71 ml, 11.7 mmol) at RT. The reaction was then stirred at RT for 72 h. Water (25 ml) was added to the reaction and stirred at RT for 20 min. The resulting biphasic solution was separated using a phase separator, the solvents were removed in vacuo and the resulting residue was subjected to flash chromatography (SiO$_2$, gradient 10 to 35% ethyl acetate in cyclohexane) to afford the title compound (1.35 g, 57%) as a white solid. $^1$H NMR (500 MHz, CDCl$_3$): δ 7.81 (2H, d), 7.38 (2H, d), 4.81 (1H, br s), 2.84 (2H, d), 3.02 (2H, br s), 1.41 (9H, s), 1.35 (12H, s), 1.19 (3H, s).

Example 2

6-(4-((1r,3r)-1-Amino-3-hydroxycyclobutyl)phenyl)-5-phenyl-3-(2,2,2-trifluoroethyl)furo[2,3-d]pyrimidin-4(3H)-one. HCl

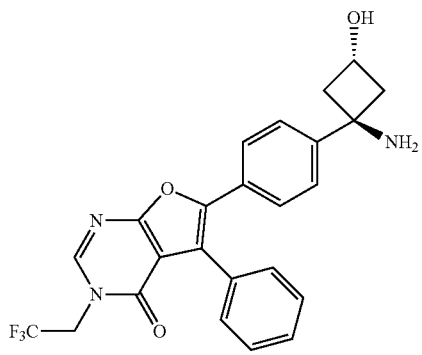 [SMILES: N[C@]1(c2ccc(-c3oc4ncn(CC(F)(F)F)c(=O)c4c3-c3ccccc3)cc2)C[C@@H](O)C1]

Step 1: tert-Butyl ((1r,3r)-3-hydroxy-1-(4-(4-oxo-5-phenyl-3-(2,2,2-trifluoroethyl)-3,4-dihydrofuro[2,3-d]pyrimidin-6-yl)phenyl)cyclobutyl)carbamate To a solution of 6-bromo-5-phenyl-3-(2,2,2-trifluoroethyl)furo[2,3-d]pyrimidin-4(3H)-one (0.075 g, 0.201 mmol) in 1,4-dioxane (2 ml) was added tert-butyl ((1r,3r)-3-hydroxy-1-(4-(4,4,5,5-tetramethyl-1,3,2-dioxaborolan-2-yl)phenyl)cyclobutyl)carbamate (0.086 g, 0.221 mmol) followed by sodium carbonate (0.064 g, 0.603 mmol) in water (1.3 ml).

The mixture was then degassed by bubbling N₂ through it before the addition of 1,1'-bis(diphenylphosphino)ferrocene-palladium(II)dichloride DCM complex (0.017 g, 0.020 mmol). The reaction mixture was heated at 70° C. for 2 h before being cooled to room temperature, diluted with DCM and water and extracted. The organic extracts were washed with brine (3×15 ml), dried (Na₂SO₄), filtered and concentrated in vacuo. The resultant residue was purified by silica gel chromatography (Biotage KP-Sil, 0 to 100% EtOAc in cyclohexane) affording the title compound as an off-white solid (105 mg, 94%). LCMS $R_T$=1.337 min, [MH]⁺−56=500. ¹H NMR (500 MHz, CDCl₃): δ 7.95 (1H, s), 7.4 (4H, m), 7.3-7.36 (3H, m), 7.2 (2H, m), 5.0 (1H, br s), 4.55-4.6 (2H, q), 4.41-4.52 (1H, m), 2.8 (2H, br s), 2.3 (2H, m), 1.2-1.3 (9H, br s).

Step 2: 6-(4-((1r,3r)-1-Amino-3-hydroxycyclobutyl)phenyl)-5-phenyl-3-(2,2,2-trifluoroethyl)furo[2,3-d]pyrimidin-4(3H)-one.HCl To a solution of tert-butyl ((1 r,3r)-3-hydroxy-1-(4-(4-oxo-5-phenyl-3-(2,2,2-trifluoroethyl)-3,4-dihydrofuro[2,3-d]pyrimidin-6-yl)phenyl)cyclobutyl)carbamate (0.105 g, 0.189 mmol) in DCM (3 ml) at 0° C. was added TFA (1 ml, 13.0 mmol). The reaction mixture was stirred at 0° C. for 2 min before being concentrated in vacuo. The residue was partitioned between DCM (15 ml) and saturated aq. NaHCO₃ (15 ml). The organic extracts were separated and dried (phase separator cartridge) and concentrated affording a beige solid. The solid was dissolved in 1,4-dioxane (2 ml) and cooled to 0° C. under N₂ before the addition of HCl in MeOH (1.3 eq, 0.5 ml). The resultant precipitate was collected, washed with 1,4-dioxane and ether and the obtained solid was dissolved in water and freeze-dried, affording the title compound as a white solid (0.049 g, 53%). LCMS $R_T$=0.737 min, [MH]⁺−17=439. ¹H NMR (500 MHz, CD₃OD): δ 8.44 (1H, s), 7.63 (2H, d), 7.39-7.51 (7H, m), 4.95 (2H, q), 4.6-4.69 (1H, m), 2.92-3.0 (2H, m), 2.58-2.66 (2H, m).

Intermediate 2: tert-Butyl((1r,3r)-3-hydroxy-1-(4-(4,4,5,5-tetramethyl-1,3,2-dioxaborolan-2-yl)phenyl)cyclobutyl)carbamate

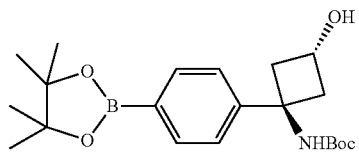 [SMILES: CC(C)(C)OC(=O)N[C@]1(c2ccc(B3OC(C)(C)C(C)(C)O3)cc2)C[C@@H](O)C1]

Step 1: (1r,3r)-3-((tert-Butoxycarbonyl)amino)-3-(4-(4,4,5,5-tetramethyl-1,3,2-dioxaborolan-2-yl)phenyl)cyclobutyl 4-nitrobenzoate In a 15 mL reaction tube was added tert-butyl((1s,3s)-3-hydroxy-1-(4-(4,4,5,5-tetramethyl-1,3,2-dioxaborolan-2-yl)phenyl)cyclobutyl)carbamate (100 mg, 0.257 mmol), 4-nitrobenzoic acid (86 mg, 0.514 mmol) and triphenylphosphine (141 mg, 0.539 mmol) in anhydrous tetrahydrofuran (1 ml). The reaction mixture was cooled to 0° C., followed by the dropwise addition of diethyl azodicarboxylate (0.085 ml, 0.539 mmol) ensuring that the temperature was maintained below 10° C. The reaction mixture was stirred at room temperature overnight. The reaction mixture was concentrated to dryness under reduced pressure and the residue was purified by column chromatography (SiO₂, gradient 0-100% ethyl acetate in cyclohexane), followed by repurification by column chromatography (SiO₂, gradient 5-40% ethyl acetate in cyclohexane) to afford the title compound as an off-white solid (50 mg, 36%). ¹H NMR (500 MHz, CDCl₃): δ 8.26 (2H, d), 8.15 (2H, d), 7.80 (2H, d), 7.38 (2H, d), 5.50-5.61 (1H, m), 5.05 (1H, br s), 2.91-3.33 (2H, br m), 2.68-2.78 (2H, m), 1.39 (9H, s), 1.34 (12H, s).

Step 2: tert-Butyl ((1r,3r)-3-hydroxy-1-(4-(4,4,5,5-tetramethyl-1,3,2-dioxaborolan-2-yl)phenyl)cyclobutyl)carbamate In a 5 ml round-bottomed flask was added (1 r,3r)-3-((tert-butoxycarbonyl)amino)-3-(4-(4,4,5,5-tetramethyl-1,3,2-dioxaborolan-2-yl)phenyl)cyclobutyl 4-nitrobenzoate (50 mg, 0.093 mmol) and potassium carbonate (19.3 mg, 0.139 mmol) in a mixture of methanol (1 ml) and water (0.1 ml). This was stirred at room temperature for 4 h. The reaction mixture was concentrated to dryness under reduced pressure. The product was redissolved with ethyl acetate (3 ml) and washed with water (3×3 ml). The organic phase was dried over Na₂SO₄, filtered and concentrated to dryness under reduced pressure to afford the title compound as a white solid (35 mg, 97%). ¹H NMR (500 MHz, MeOD) δ 7.69 (2H, d), 7.37 (2H, d), 4.40 (1H, p), 2.79-2.93 (2H, br m), 2.25-2.33 (2H, m), 1.30-1.43 (21H, br m).

Example 3

6-(4-((1s,3s)-1-Amino-3-hydroxycyclobutyl)phenyl)-5-phenyl-3-(2,2,2-trifluoroethyl)furo[2,3-d]pyrimidin-4(3H)-one.HCl

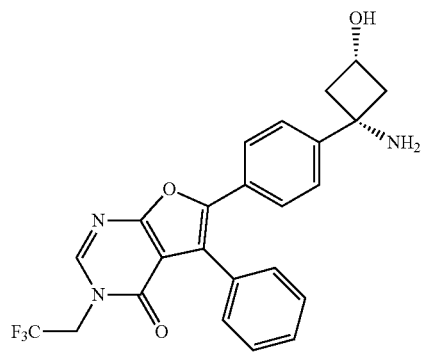 [SMILES: N[C@]1(c2ccc(-c3oc4ncn(CC(F)(F)F)c(=O)c4c3-c3ccccc3)cc2)C[C@H](O)C1]

Step 1: tert-Butyl((1s,3s)-3-hydroxy-1-(4-(4-oxo-5-phenyl-3-(2,2,2-trifluoroethyl)-3,4-dihydrofuro[2,3-d]pyrimidin-6-yl)phenyl)cyclobutyl)carbamate: Following the procedure for tert-butyl ((1r,3r)-3-hydroxy-1-(4-(4-oxo-5-phenyl-3-(2,2,2-trifluoroethyl)-3,4-dihydrofuro[2,3-d]pyrimidin-6-yl)phenyl)cyclobutyl)carbamate (Example 2, Step 1), 6-bromo-5-phenyl-3-(2,2,2-trifluoroethyl)furo[2,3-d]pyrimidin-4(3H)-one (0.050 g, 0.134 mmol) and tert-butyl((1s,3s)-3-hydroxy-1-(4-(4,4,5,5-tetramethyl-1,3,2-dioxaborolan-2-yl)phenyl)cyclobutyl)carbamate (0.057 g, 0.147 mmol, prepared as described in WO2011/77098) were reacted to afford the title compound as a gum (45 mg, 60%). LCMS $R_T$=1.32 min, [MH]⁺−117=439. ¹H NMR (500 MHz, CDCl₃): δ 7.98 (1H, s), 7.4-7.5 (4H, m), 7.3-7.36 (3H, m), 7.25 (2H, d), 4.55-4.62 (2H, q), 4.05 (1H, m), 2.96 (2H, br s), 2.6 (2H, br s), 1.3 (9H, br s).

Step 2: 6-(4-((1s,3s)-1-Amino-3-hydroxycyclobutyl)phenyl)-5-phenyl-3-(2,2,2-trifluoroethyl)furo[2,3-d]pyrimidin-4(3H)-one hydrochloride Following the procedure for 6-(4-((1r,3r)-1-amino-3-hydroxycyclobutyl)phenyl)-5-phenyl-3-(2,2,2-trifluoroethyl)furo[2,3-d]pyrimidin-4(3H)-one hydrochloride (Example 2, step 2), tert-butyl((1s,3s)-3-hydroxy-1-(4-(4-oxo-5-phenyl-3-(2,2,2-trifluoroethyl)-3,4-dihydrofuro[2,3-d]pyrimidin-6-yl)phenyl)cyclobutyl)carbamate (0.045 g, 0.081 mmol) was deprotected affording the title compound as a white solid (7 mg, 17%). LCMS $R_T$=0.783 min, [MH]$^+$−17=439. $^1$H NMR (500 MHz, CD$_3$OD): δ 8.29 (1H, s), 7.39-7.42 (9H, m), 4.8 (2H, q), 3.8 (1H, m), 2.83 (2H, m), 2.1 (2H, m).

Example 4

6-(4-((1r,3r)-1-Amino-3-hydroxy-3-methylcyclobutyl)phenyl)-5-phenyl-3-(2,2,2-trifluoroethyl)furo[2,3-d]pyrimidin-4(3H)-one.HCl

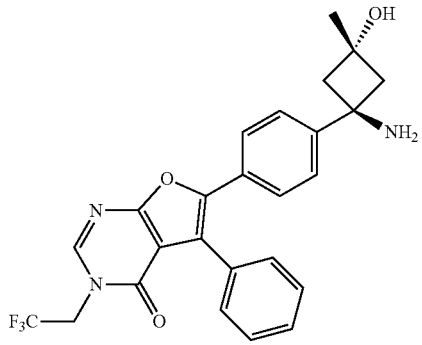 [SMILES: C[C@]1(O)C[C@@](N)(c2ccc(-c3oc4ncn(CC(F)(F)F)c(=O)c4c3-c3ccccc3)cc2)C1]

Step 1: tert-Butyl ((1r,3r)-3-hydroxy-3-methyl-1-(4-(4-oxo-5-phenyl-3-(2,2,2-trifluoroethyl)-3,4-dihydrofuro[2,3-d]pyrimidin-6-yl)phenyl)cyclobutyl)carbamate Following the procedure for tert-butyl ((1r,3r)-3-hydroxy-1-(4-(4-oxo-5-phenyl-3-(2,2,2-trifluoroethyl)-3,4-dihydrofuro[2,3-d]pyrimidin-6-yl)phenyl)cyclobutyl)carbamate (Example 2, Step 1), 6-bromo-5-phenyl-3-(2,2,2-trifluoroethyl)furo[2,3-d]pyrimidin-4(3H)-one (0.1 g, 0.268 mmol) and tert-butyl ((1r,3r)-3-hydroxy-3-methyl-1-(4-(4,4,5,5-tetramethyl-1,3,2-dioxaborolan-2-yl)phenyl)cyclobutyl)carbamate (0.11 g, 0.268 mmol) were reacted to afford the title compound as an off-white solid (75 mg, 49%). LCMS $R_T$=1.39 min, [MH]$^+$−56=514. $^1$H NMR (500 MHz, CDCl$_3$): δ 8.06 (1H, s), 7.5-7.55 (4H, m), 7.43 (3H, m), 7.35 (2H, d), 5.0 (1H, br s), 4.65-4.72 (2H, q), 2.65 (4H, br s), 1.4 (9H, br s).

Step 2: 6-(4-((1r,3r)-1-Amino-3-hydroxy-3-methylcyclobutyl)phenyl)-5-phenyl-3-(2,2,2-trifluoroethyl)furo[2,3-d]pyrimidin-4(3H)-one.HCl Following the procedure for 6-(4-((1r,3r)-1-amino-3-hydroxycyclobutyl)phenyl)-5-phenyl-3-(2,2,2-trifluoroethyl)furo[2,3-d]pyrimidin-4(3H)-one hydrochloride (Example 2, Step 2), tert-butyl ((1r,3r)-3-hydroxy-3-methyl-1-(4-(4-oxo-5-phenyl-3-(2,2,2-trifluoroethyl)-3,4-dihydrofuro[2,3-d]pyrimidin-6-yl)phenyl)cyclobutyl)carbamate (0.075 g, 0.132 mmol) was deprotected affording the title compound as a white solid (31 mg, 47%). LCMS $R_T$=0.7 min, [MH]$^+$−17=453. $^1$H NMR (500 MHz, CD$_3$OD): δ 8.31 (1H, s), 7.5 (2H, d), 7.42 (2H, d), 7.3-7.4 (5H, m), 4.75 (2H, q), 2.75 (2H, d), 2.6 (2H, d), 1.39 (3H, s).

Example 5

6-(4-((1r,3r)-1-Amino-3-hydroxy-3-methylcyclobutyl)phenyl)-5-phenyl-3-(2,2,2-trifluoroethyl)thieno[2,3-d]pyrimidin-4(3H)-one.TFA

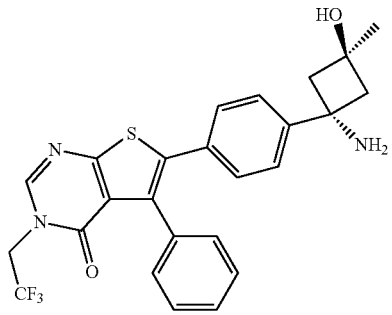 [SMILES: C[C@]1(O)C[C@@](N)(c2ccc(-c3sc4ncn(CC(F)(F)F)c(=O)c4c3-c3ccccc3)cc2)C1]

Step 1: 5-Phenyl-3-(2,2,2-trifluoroethyl)thieno[2,3-d]pyrimidin-4(3H)-one

A mixture of 5-phenylthieno[2,3-d]pyrimidin-4(3H)-one (20 g, 88 mmol), 1,1,1-trifluoro-2-iodoethane (36.8 g, 175 mmol) and potassium carbonate (26.6 g, 193 mmol) in DMF (100 ml) was heated at 70° C. for 0.5 h and at 100° C. for 2 h. A further portion of 1,1,1-trifluoro-2-iodoethane (36.8 g, 175 mmol) was added and the resulting mixture was heated at 100° C. for a further 16 h. The reaction mixture was cooled down and diluted with water (750 ml) and the precipitate was filtered to give the title compound as a light yellow solid (13 g, 48%). LCMS $R_T$=1.30 min, M+H$^+$=311.1.

Step 2: 6-Bromo-5-phenyl-3-(2,2,2-trifluoroethyl)thieno[2,3-d]pyrimidin-4(3H)-one A mixture of 5-phenyl-3-(2,2,2-trifluoroethyl)thieno[2,3-d]pyrimidin-4(3H)-one (0.4 g, 1.29 mmol) and NBS (0.459 g, 2.58 mmol) in DMF (5 ml) was heated at 80° C. for 2 h. The reaction mixture was diluted with water (40 ml) and extracted with DCM (3×25 ml). The combined organic phases were washed with water (3×45 ml) and brine (30 ml), dried and concentrated to give the title compound (0.46 g, 91%). LCMS $R_T$=1.46 min, M+H$^+$=390.9/392.9.

Step 3: tert-Butyl ((1r,3r)-3-hydroxy-3-methyl-1-(4-(4-oxo-5-phenyl-3-(2,2,2-trifluoroethyl)-3,4-dihydrothieno[2,3-d]pyrimidin-6-yl)phenyl)cyclobutyl)carbamate A mixture of tert-butyl ((1r,3r)-3-hydroxy-3-methyl-1-(4-(4,4,5,5-tetramethyl-1,3,2-dioxaborolan-2-yl)phenyl)cyclobutyl)carbamate (155 mg, 0.385 mmol), 6-bromo-5-phenyl-3-(2,2,2-trifluoroethyl)thieno[2,3-d]pyrimidin-4(3H)-one (150 mg, 0.385 mmol) and cesium carbonate (628 mg, 1.93 mmol) in dioxane (6 ml) and water (2 ml) was degassed by bubbling nitrogen through the reaction mixture for 5 min. Pd(dppf)Cl$_2$.CH$_2$Cl$_2$ (62.9 mg, 0.077 mmol) was added and the resulting mixture was degassed by bubbling nitrogen through the reaction mixture for 5 min then heated at 55° C. for 3 h. The organic phase of the reaction mixture was separated, concentrated in vacuo and purified by silica gel chromatography (gradient 0-75% ethyl acetate in cyclohexane) to afford the title product (0.15 g, 66%). LCMS $R_T$=1.40 min, M+H$^+$=586.2.

Step 4: 6-(4-((1r,3r)-1-Amino-3-hydroxy-3-methylcyclobutyl)phenyl)-5-phenyl-3-(2,2,2-trifluoroethyl)thieno[2,3-d]pyrimidin-4(3H)-one.TFA tert-Butyl ((1r,3r)-3-hydroxy-3-methyl-1-(4-(4-oxo-5-phenyl-3-(2,2,2-trifluoroethyl)-3,4-dihydrothieno[2,3-d]pyrimidin-6-yl)phenyl)cyclobutyl)carbamate (100 mg, 0.171 mmol) was dissolved in TFA (1 ml) and stirred for 30 seconds. The solution was immediately concentrated to dryness under reduced pressure. The residue was then slurried in diethyl ether (2 ml) and after settling the supernatant solvent removed by pipette. This was repeated twice. The remaining solvent was removed under reduced pressure and dried to give the desired product (70 mg) as a white solid. LCMS $R_T$=0.77 min, M+H$^+$=486.1. $^1$H NMR (500 MHz, CD$_3$OD) δ 8.39 (1H, s), 7.48 (2H, d), 7.20-7.40 (7H, m), 4.8 (2H, q), 2.89 (2H, d), 2.71 (2H, d), 1.52 (3H, s).

Example 6

6-(4-((1r,3r)-1-Amino-3-hydroxy-3-methylcyclobutyl)phenyl)-7-methyl-5-phenyl-3-(2,2,2-trifluoroethyl)-3H-pyrrolo[2,3-d]pyrimidin-4(7H)-one.HCl

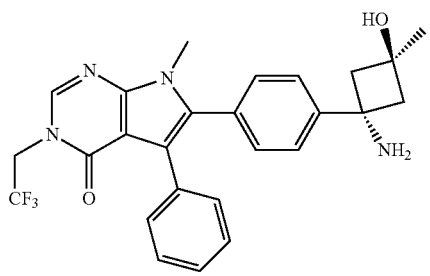 [SMILES: Cn1c(-c2ccc([C@]3(N)C[C@](C)(O)C3)cc2)c(-c2ccccc2)c2c(=O)n(CC(F)(F)F)cnc21]

Step 1: 4-Chloro-5-iodo-7-methyl-7H-pyrrolo[2,3-d]pyrimidine

To a stirred solution of 4-chloro-7H-pyrrolo[2,3-d]pyrimidine (2 g, 13.0 mmol) in anhydrous DMF (40 ml) was added potassium hydroxide (2.19 g, 39.1 mmol) followed by iodine (3.64 g, 14.3 mmol). The mixture was stirred for 1 h. Methyl iodide (0.814 ml, 13.0 mmol) was added and the mixture stirred for a further 1 h. The mixture was poured into 20% w/w sodium thiosulfate solution (400 ml). The formed solid was collected by filtration and dried under vacuum to afford the title compound which was used in the next step without further purification. LCMS $R_T$=1.12 min, [M($^{35}$Cl)+H]$^+$=294.0, [M($^{37}$Cl)+H]$^+$=295.9.

Step 2: 4-Chloro-7-methyl-5-phenyl-7H-pyrrolo[2,3-d]pyrimidine

A stirred suspension of 4-chloro-5-iodo-7-methyl-7H-pyrrolo[2,3-d]pyrimidine (3.31 g, 11.3 mmol), tetramethyl-2-phenyl-1,3,2-dioxaborolane (2.76 g, 13.53 mmol) and sodium carbonate (3.59 g, 33.8 mmol) in 1,4-dioxane (90 ml) and water (18.0 ml) was degassed by bubbling N$_2$ through it for 10 min. 1,1'-Bis(diphenylphosphino)ferrocenedichloro palladium(II) dichloromethane complex (0.921 g, 1.13 mmol) was then added and the reaction mixture degassed with N$_2$ again for 10 min before heating at 70° C. for 2 h. The solvent was removed in vacuo and the residue partitioned between saturated sodium hydrogen carbonate (90 ml) and dichloromethane (90 ml). The layers were separated and the aqueous phase extracted with dichloromethane (3×45 ml). The combined organic phases were dried (phase separator cartridge) and concentrated in vacuo. The resulting residue was purified by silica gel chromatography (gradient 0-50% ethyl acetate in cyclohexane) to afford the title compound (1.32 g, 48%). LCMS $R_T$=1.26 min, [M($^{35}$Cl)+H]$^+$=244.1, [M($^{37}$Cl)+H]$^+$=246.1.

Step 3: 7-Methyl-5-phenyl-3H-pyrrolo[2,3-d]pyrimidin-4(7H)-one

To a stirred solution of 4-chloro-7-methyl-5-phenyl-7H-pyrrolo[2,3-d]pyrimidine (1.32 g, 5.42 mmol) in 1,4-dioxane (40 ml) was added 2M sodium hydroxide (aq) solution (40 ml, 80 mmol). The solution was heated to 100° C. for 16 h. The solution was cooled and the organic solvent removed in vacuo. The aqueous mixture was extracted using ethyl acetate (3×40 ml) and the organic extract was discarded. The solid was collected and dried using a sintered funnel under vacuum to afford the title compound (0.86 g, 71%) which was used in the next step without further purification. LCMS $R_T$=0.87 min, M+H$^+$=226.1.

Step 4: 7-Methyl-5-phenyl-3-(2,2,2-trifluoroethyl)-3H-pyrrolo[2,3-d]pyrimidin-4(7H)-one To a stirring suspension of 7-methyl-5-phenyl-3H-pyrrolo[2,3-d]pyrimidin-4(7H)-one (0.86 g, 3.82 mmol) in anhydrous DMF (30 ml) was added potassium carbonate (1.06 g, 7.64 mmol) and 1,1,1-trifluoro-2-iodoethane (0.564 ml, 5.73 mmol). The mixture was heated to 90° C. for 16 h. A further portion of potassium carbonate (1.06 g, 7.64 mmol) and 1,1,1-trifluoro-2-iodoethane (0.564 ml, 5.73 mmol) were added and the mixture heated to 90° C. for 24 h. The mixture was cooled and partitioned between brine/water (1:1, 300 ml) and ethyl acetate (75 ml). The aqueous portion was separated and extracted with ethyl acetate (3×75 ml). The combined organic fractions were washed with brine/water (1:1, 4×75 ml), dried (anhydrous sodium sulfate), filtered and concentrated in vacuo. The residue was purified by silica gel chromatography (gradient 0-30% ethyl acetate in cyclohexane) to afford the title compound (719 mg, 61%). LCMS $R_T$=1.25 min, M+H$^+$=308.0.

Step 5: 6-Bromo-7-methyl-5-phenyl-3-(2,2,2-trifluoroethyl)-3H-pyrrolo[2,3-d]pyrimidin-4(7H)-one To a stirring solution of 7-methyl-5-phenyl-3-(2,2,2-trifluoroethyl)-3H-pyrrolo[2,3-d]pyrimidin-4(7H)-one (825 mg, 2.68 mmol) in anhydrous DMF (6 ml) at 0° C. was added bromine (0.152 ml, 2.95 mmol) and the mixture stirred for 30 min. The mixture was partitioned between ethyl acetate (50 ml) and an aqueous mixture (water, saturated sodium hydrogen carbonate solution and 20% w/w sodium thiosulfate solution, 3:1:4; 100 ml). The aqueous phase was separated and extracted using ethyl acetate (3×25 ml). The combined ethyl acetate fractions were washed with brine/water (1:1, 4×25 ml), dried (anhydrous sodium sulfate), filtered and reduced in vacuo. The resulting residue was purified by silica gel chromatography (gradient 0-40% ethyl acetate in cyclohexane) to afford the title compound (0.97 g, 94%). LCMS $R_T$=1.40 min, M+H⁺=385.9/388.0.

Step 6: tert-Butyl ((1r,3r)-3-hydroxy-3-methyl-1-(4-(7-methyl-4-oxo-5-phenyl-3-(2,2,2-trifluoroethyl)-4,7-dihydro-3H-pyrrolo[2,3-d]pyrimidin-6-yl)phenyl)cyclobutyl)carbamate A stirred suspension of 6-bromo-7-methyl-5-phenyl-3-(2,2,2-trifluoroethyl)-3H-pyrrolo[2,3-d]pyrimidin-4(7H)-one (100 mg, 0.259 mmol), tert-butyl ((1r,3r)-3-hydroxy-3-methyl-1-(4-(4,4,5,5-tetramethyl-1,3,2-dioxaborolan-2-yl)phenyl)cyclobutyl)carbamate (125 mg, 0.311 mmol) and sodium carbonate (82 mg, 0.777 mmol) in 1,4-dioxane (4 ml) and water (0.800 ml) was degassed by bubbling $N_2$ through it for 5 min. 1,1'-Bis(diphenylphosphino)ferrocenedichloropalladium(II) dichloromethane complex (21.2 mg, 0.026 mmol) was added and the reaction mixture degassed again with $N_2$ for 5 min before heating at 70° C. for 16 h. The solvent was removed in vacuo and the residue partitioned between saturated sodium hydrogen carbonate (6 ml) and dichloromethane (6 ml). The layers were separated and the aqueous phase extracted with dichloromethane (3×6 ml). The combined organic phases were dried (phase separator cartridge), filtered and concentrated in vacuo. The resulting residue was purified by silica gel chromatography (gradient 0-60% ethyl acetate in cyclohexane). The material was re-purified by silica gel chromatography (gradient 0-7% methanol in dichloromethane) to afford the title compound (74 mg, 49%). LCMS $R_T$=1.37 min, M+H⁺=583.2.

Step 7: 6-(4-((1 r,3r)-1-Amino-3-hydroxy-3-methylcyclobutyl)phenyl)-7-methyl-5-phenyl-3-(2,2,2-trifluoroethyl)-3H-pyrrolo[2,3-d]pyrimidin-4(7H)-one.HCl To a stirred solution of tert-butyl ((1r,3r)-3-hydroxy-3-methyl-1-(4-(7-methyl-4-oxo-5-phenyl-3-(2,2,2-trifluoroethyl)-4,7-dihydro-3H-pyrrolo[2,3-d]pyrimidin-6-yl)phenyl)cyclobutyl)carbamate (73.5 mg, 0.126 mmol) in anhydrous dichloromethane (2 ml) at 0° C. was added trifluoroacetic acid (1 ml, 13.0 mmol). The mixture was stirred for 1.5 h while warming to room temperature. The solution was concentrated in vacuo. The residue was azeotroped twice with dichloromethane (2 ml). An SCX-2 silica cartridge was pre-treated with 20% v/v methanol in dichloromethane (100 ml). The residue was dissolved in dichloromethane (3 ml) and placed on to the SCX-2 column. After 30 min, the column was flushed with 20% v/v methanol in dichloromethane (100 ml) followed by 20% v/v (7M ammonia in methanol) in dichloromethane (50 ml). The ammonia containing fraction was reduced in vacuo. The residue was dissolved in methanol (4 ml). A solution of HCl in methanol (29 uL of acetyl chloride added to 0.5 ml of methanol) was added. After 10 min, the methanol was reduced to ca 1 ml in vacuo. Diethyl ether (20 ml) was added and the resulting suspension stirred for 10 min. The precipitate was collected by vacuum filtration under flowing nitrogen. The wet cake was washed with diethyl ether (2×5 ml), dissolved in water (5 ml), filtered and freeze-dried to afford the title compound (48.3 mg, 74%). LCMS $R_T$=0.77 min, M+H⁺=483.1. ¹H NMR (500 MHz, CD₃OD) δ 8.23 (1H, s), 7.59 (2H, d), 7.44 (2H, d), 7.23-7.26 (2H, m), 7.14-7.17 (3H, m), 4.86 (2H, q), 3.68 (3H, s), 2.90 (2H, d), 2.72 (2H, d), 1.51 (3H, s).

Example 7

6-(4-((1s,3s)-1-Amino-3-hydroxycyclobutyl)phenyl)-7-methyl-5-phenyl-3-(2,2,2-trifluoroethyl)-3H-pyrrolo[2,3-d]pyrimidin-4(7H)-one.HCl

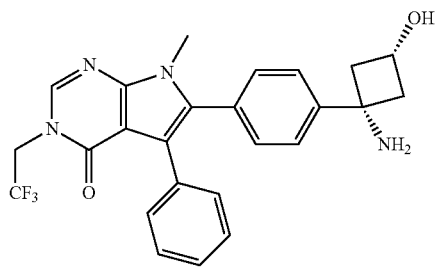 [SMILES: Cn1c(-c2ccc([C@]3(N)C[C@@H](O)C3)cc2)c(-c2ccccc2)c2c(=O)n(CC(F)(F)F)cnc21]

Step 1: tert-Butyl((1s,3s)-3-hydroxy-1-(4-(7-methyl-4-oxo-5-phenyl-3-(2,2,2-trifluoroethyl)-4,7-dihydro-3H-pyrrolo[2,3-d]pyrimidin-6-yl)phenyl)cyclobutyl)carbamate A stirring suspension of 6-bromo-7-methyl-5-phenyl-3-(2,2,2-trifluoroethyl)-3H-pyrrolo[2,3-d]pyrimidin-4(7H)-one (100 mg, 0.259 mmol), tert-butyl((1s,3s)-3-hydroxy-1-(4-(4,4,5,5-tetramethyl-1,3,2-dioxaborolan-2-yl)phenyl)cyclobutyl)carbamate (121 mg, 0.311 mmol) and sodium carbonate (82 mg, 0.777 mmol) in 1,4-dioxane (4 ml) and water (0.8 ml) was degassed by bubbling $N_2$ through it for 5 mins. 1,1'-Bis(diphenylphosphino)ferrocenedichloro palladium (II) dichloromethane complex (21.2 mg, 0.026 mmol) was then added and the reaction mixture degassed again with $N_2$ for 5 min before heating at 70° C. for 16 h. The solvent was removed in vacuo and the residue partitioned between saturated sodium hydrogen carbonate (6 ml) and dichloromethane (6 ml). The layers were separated and the aqueous phase extracted with dichloromethane (3×6 ml). The combined organic phases were dried (phase separator cartridge), filtered and concentrated in vacuo. The resulting residue was purified by silica gel chromatography (gradient 0-60% ethyl acetate in cyclohexane), followed by repurification by silica gel chromatography (gradient 0-5% methanol in dichloromethane) This material was re-purified by silica gel chromatography (gradient 0-60% ethyl acetate in dichloromethane) to afford the title compound (39.5 mg, 27%). LCMS $R_T$=1.30 min, M+H⁺=569.1.

Step 2: 6-(4-((1s,3s)-1-Amino-3-hydroxycyclobutyl)phenyl)-7-methyl-5-phenyl-3-(2,2,2-trifluoroethyl)-3H-pyrrolo[2,3-d]pyrimidin-4(7H)-one.HCl To a stirred solution of tert-butyl ((1s,3s)-3-hydroxy-1-(4-(7-methyl-4-oxo-5-phenyl-3-(2,2,2-trifluoroethyl)-4,7-dihydro-3H-pyrrolo[2,3-d]pyrimidin-6-yl)phenyl)cyclobutyl)carbamate (39.5 mg, 0.069 mmol) in anhydrous dichloromethane (2 ml) at 0° C. was added trifluoroacetic acid (0.5 ml, 6.49 mmol). The mixture was stirred for 1 h whilst warming to room temperature. The solution was reduced in vacuo. The residue was azeotroped twice with dichloromethane (2 ml). An SCX-2 silica cartridge (5 g) was pretreated with 20% v/v methanol in dichloromethane (50 ml). The azeotroped residue was dissolved in dichloromethane (3×1 ml) and placed on to the SCX-2 column. After 1.5 h the column was flushed with 20% v/v methanol in dichloromethane (50 ml) followed by 20% v/v (7M ammonia in methanol) in dichloromethane (25 ml). The ammonia containing fraction was reduced in vacuo. The residue was dissolved in hot 1,4-dioxane (4 ml). A solution of HCl in methanol (24 uL of acetyl chloride added to 1 ml of methanol) was added. After 10 min, diethyl ether (20 ml) was added and the resulting suspension stirred for 10 min. The precipitate was collected by vacuum filtration under flowing nitrogen. The wet cake was washed with diethyl ether (2×5 ml), dissolved in water (12 ml), filtered and freeze-dried to afford the title compound (28.3 mg, 81%). LCMS $R_T$=0.80 min, M+H$^+$=469.1. $^1$H NMR (500 MHz, CD$_3$OD) δ 8.23 (1H, s), 7.58 (2H, d), 7.44 (2H, d), 7.23-7.25 (2H, m), 7.15-7.17 (3H, m), 4.88 (2H, q), 4.10 (1H, q), 3.69 (3H, s), 3.09-3.13 (2H, m), 2.47-2.51 (2H, m).

Example 8

6-(4-((1s,3s)-1-Amino-3-hydroxy-3-methylcyclobutyl)phenyl)-5-phenyl-3-(2,2,2-trifluoroethyl)thieno[2,3-d]pyrimidin-4(3H)-one.HCl

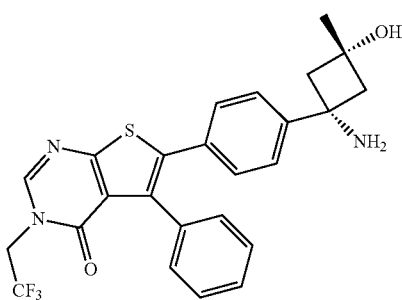 [SMILES: C[C@]1(O)C[C@](N)(c2ccc(-c3sc4ncn(CC(F)(F)F)c(=O)c4c3-c3ccccc3)cc2)C1]

Step 1: 2-((1s,3s)-3-Hydroxy-3-methyl-1-(4-(4-oxo-5-phenyl-3-(2,2,2-trifluoroethyl)-3,4-dihydrothieno[2,3-d]pyrimidin-6-yl)phenyl)cyclobutyl)isoindoline-1,3-dione A mixture of 6-bromo-5-phenyl-3-(2,2,2-trifluoroethyl)thieno[2,3-d]pyrimidin-4(3H)-one (150 mg, 0.385 mmol), 2-((1s,3s)-3-hydroxy-3-methyl-1-(4-(4,4,5,5-tetramethyl-1,3,2-dioxaborolan-2-yl)phenyl)cyclobutyl)isoindoline-1,3-dione (167 mg, 0.385 mmol), and cesium carbonate (628 mg, 1.93 mmol) in dioxane (6 ml) and water (2 ml) was degassed by bubbling nitrogen through the reaction for 5 min. Pd(dppf)Cl$_2$.CH$_2$Cl$_2$ (62.9 mg, 0.077 mmol) was added. The reaction mixture, after degassing, was heated at 55° C. for 3 h. The organic phase of the reaction mixture was separated, concentrated in vacuo and purified by silica gel chromatography (gradient 0-100% ethyl acetate in cyclohexane) to afford the title product (84 mg, 35%). LCMS $R_T$=1.44 min, M+H$^+$=616.1.

Step 2: 6-(4-((1s,3s)-1-Amino-3-hydroxy-3-methylcyclobutyl)phenyl)-5-phenyl-3-(2,2,2-trifluoroethyl)thieno[2,3-d]pyrimidin-4(3H)-one.HCl A mixture of 2-((1s,3s)-3-hydroxy-3-methyl-1-(4-(4-oxo-5-phenyl-3-(2,2,2-trifluoroethyl)-3,4-dihydrothieno[2,3-d]pyrimidin-6-yl)phenyl)cyclobutyl)isoindoline-1,3-dione (80 mg, 0.13 mmol) and hydrazine hydrate (0.5 ml, 10.2 mmol) in 1,4-dioxane (2 ml) and MeOH (2 ml) was heated under microwave conditions at 100° C. for 20 min. The reaction mixture was partitioned between DCM (10 ml) and sodium bicarbonate solution (10 ml). The organic phase was washed with sodium bicarbonate solution (2×10 ml), brine and concentrated in vacuo. The residue was purified by silica gel chromatography (gradient 0-10% methanol in DCM) to give the product (26 mg) which was redissolved in DCM (20 ml) and acidified with HCl in ether (2M, 2 eq.). The suspension was concentrated and freeze-dried to give the title compound (25 mg) as a white solid. LCMS $R_T$=0.866 min, M+H$^+$=486.1. $^1$H NMR (500 MHz, CD$_3$OD) δ 8.27 (1H, s), 7.13-7.30 (9H, m), 4.75 (2H, q), 2.7 (2H, d), 2.5 (2H, d), 1.1 (3H, s).

Example 9

6-(4-((1s,3s)-1-Amino-3-hydroxycyclobutyl)phenyl)-5-phenyl-3-(2,2,2-trifluoroethyl)thieno[2,3-d]pyrimidin-4(3H)-one.HCl

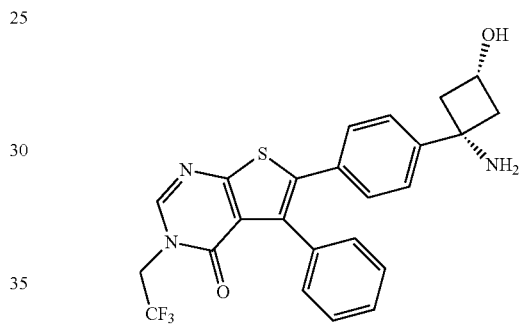

Step 1: tert-Butyl((1s,3s)-3-hydroxy-1-(4-(4-oxo-5-phenyl-3-(2,2,2-trifluoroethyl)-3,4-dihydrothieno[2,3-d]pyrimidin-6-yl)phenyl)cyclobutyl)carbamate A mixture of 6-bromo-5-phenyl-3-(2,2,2-trifluoroethyl)thieno[2,3-d]pyrimidin-4(3H)-one (150 mg, 0.385 mmol), tert-butyl((1s,3s)-3-hydroxy-1-(4-(4,4,5,5-tetramethyl-1,3,2-dioxaborolan-2-yl)phenyl)cyclobutyl)carbamate (165 mg, 0.424 mmol) and cesium carbonate (628 mg, 1.93 mmol) in dioxane (6 ml) and water (2 ml) was degassed by bubbling nitrogen through the reaction mixture for 5 min. Pd(dppf)Cl2.CH2Cl2 (62.9 mg, 0.077 mmol) was added. The resulting mixture was degassed again, and heated at 55° C. for 4 h. The reaction mixture was cooled to RT, diluted with water (30 ml) and extracted with DCM (3×20 ml). The combined organic phase was washed with water, dried with sodium sulfate and concentrated in vacuo. The residue was purified by silica gel chromatography (gradient 0-100% ethyl acetate in cyclohexane) to afford the title product (96 mg, 44%). LCMS RT=1.34 min, M+H$^+$=572.

Step 2: 6-(4-((1s,3s)-1-Amino-3-hydroxycyclobutyl)phenyl)-5-phenyl-3-(2,2,2-trifluoroethyl)thieno[2,3-d]pyrimidin-4(3H)-one.HCl To tert-butyl ((1s,3s)-3-hydroxy-1-(4-(4-oxo-5-phenyl-3-(2,2,2-trifluoroethyl)-3,4-dihydrothieno[2,3-d]pyrimidin-6-yl)phenyl)cyclobutyl)carbamate (90 mg, 0.157 mmol) was charged TFA (1 ml) and the mixture was stirred for 30 seconds at RT. The solution was immediately concentrated to dryness under reduced pressure. The residue was then slurried in diethyl ether (2 ml) and after the suspension had settled, the supernatant solvent was removed by pipette. This process was repeated twice. The solid was dried under reduced pressure to give the crude product. The material was partitioned between DCM (15 ml) and sodium bicarbonate solution (15 ml). The organic phase was separated and concentrated. The residue was purified by column chromatography (The column was pretreated with 2 volume 7M methanol/DCM 1:1) eluted with methanol/DCM 0-10% to give the product as the free base (28 mg) which was redissolved in DCM (25 ml). HCl in ether (2M, 2 eq) was added and the resulting suspension was concentrated and freeze dried to give the title compound (19 mg) as a white solid. LCMS $R_T$=0.809 min, M+H$^+$=473. $^1$H NMR (500 MHz, CD$_3$OD) δ 8.26 (1H, s), 7.35 (2H, d), 7.20-7.30 (7H, m), 4.8 (2H, q), 3.95 (1H, m), 2.95 (2H, m), 2.34 (2H, m).

Example 10

6-(4-((1s,3s)-1-Amino-3-hydroxy-3-methylcyclobutyl)phenyl)-7-methyl-5-phenyl-3-(2,2,2-trifluoroethyl)-3H-pyrrolo[2,3-d]pyrimidin-4(7H)-one.HCl

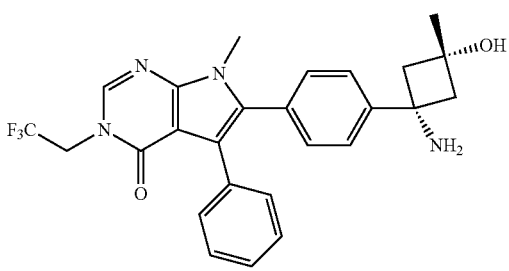 [SMILES: Cn1c(-c2ccc([C@]3(N)C[C@@](C)(O)C3)cc2)c(-c2ccccc2)c2c(=O)n(CC(F)(F)F)cnc21]

Step 1: 2-((1s,3s)-3-Hydroxy-3-methyl-1-(4-(7-methyl-4-oxo-5-phenyl-3-(2,2,2-trifluoroethyl)-4,7-dihydro-3H-pyrrolo[2,3-d]pyrimidin-6-yl)phenyl)cyclobutyl)isoindoline-1,3-dione To a solution of 6-bromo-7-methyl-5-phenyl-3-(2,2,2-trifluoroethyl)-3H-pyrrolo[2,3-d]pyrimidin-4(7H)-one (60 mg, 0.155 mmol), 2-((1s,3s)-3-hydroxy-3-methyl-1-(4-(4,4,5,5-tetramethyl-1,3,2-dioxaborolan-2-yl)phenyl)cyclobutyl)isoindoline-1,3-dione (81 mg, 0.186 mmol) and cesium carbonate (152 mg, 0.466 mmol) were added in 1,4-dioxane (5 ml) and water (1.25 ml). The reaction mixture was degassed by bubbling nitrogen through the reaction mixture for 5 min. 1,1'-Bis(diphenylphosphino)ferrocene-palladium(II)dichloride dichloromethane complex (25.4 mg, 0.031 mmol) was added, then the reaction was degassed with nitrogen for 5 min. The reaction mixture was stirred at 60° C. for 5 h under atmosphere of nitrogen. After allowing to cool to RT, the reaction mixture was concentrated in vacuo and the residue partitioned between water and ethyl acetate. The organic layer was washed with brine (50 ml), dried (Na$_2$SO$_4$), filtered, concentrated in vacuo, and the resulting residue was subjected to flash chromatography (SiO$_2$, gradient 0 to 50% ethyl acetate in cyclohexane) to afford the title compound (65 mg, 68%). LCMS $R_T$=1.37 min, M+H$^+$=613. $^1$H NMR (500 MHz, CDCl$_3$): δ 7.94 (1H, s), 7.75-7.82 (4H, m), 7.70-7.75 (2H, m), 7.25-7.30 (4H, m), 7.15-7.18 (3H, m), 4.67-4.74 (2H, m), 4.12-4.17 (1H, m), 3.66 (3H, s), 3.35-3.40 (2H, m), 3.10-3.17 (2H, m), 1.16 (3H, s).

Step 2: 6-(4-((1s,3s)-1-Amino-3-hydroxy-3-methylcyclobutyl)phenyl)-7-methyl-5-phenyl-3-(2,2,2-trifluoroethyl)-3H-pyrrolo[2,3-d]pyrimidin-4(7H)-one. HCl In a sealable tube was added 2-((1s,3s)-3-hydroxy-3-methyl-1-(4-(7-methyl-4-oxo-5-phenyl-3-(2,2,2-trifluoroethyl)-4,7-dihydro-3H-pyrrolo[2,3-d]pyrimidin-6-yl)phenyl)cyclobutyl)isoindoline-1,3-dione (60 mg, 0.098 mmol) and hydrazine hydrate (0.143 mL, 2.94 mmol) in methanol (2.5 mL) and water (2.5 mL). The tube was sealed and the reaction was heated at 120° C. for 30 min under microwave conditions (Biotage). The solvent was removed in vacuo. A SCX-2 silica cartridge was pre-treated with 20% v/v methanol in dichloromethane (100 ml). The residue was dissolved in dichloromethane (3×2 ml) and placed on to the SCX-2 column. The column was flushed with 20% v/v methanol in dichloromethane (100 ml) followed by 20% v/v 7M ammonia (in methanol) in dichloromethane (50 ml). The ammonia containing fraction was reduced in vacuo. The residue was dissolved in methanol (5 ml). A solution of HCl in methanol (3 µl of acetyl chloride added to 200 µl of methanol) was added. After 10 min the methanol was reduced in vacuo, dissolved in water (50 ml) and freeze-dried to afford the title compound (20 mg, 40%). LCMS $R_T$=0.90 min, M+H$^+$=483. $^1$H NMR (500 MHz, CD$_3$OD): δ 8.25 (1H, s), 7.54-7.58 (2H, m), 7.44-7.48 (2H, m), 7.24-7.27 (2H, m), 7.16-7.19 (3H, m), 3.71 (3H, s), 2.89 (2H, d), 2.70 (2H, d), 2.00 (3H, s), 1.25 (3H, s).

Example 11

6-(4-((1r,3r)-1-Amino-3-hydroxycyclobutyl)phenyl)-7-methyl-5-phenyl-3-(2,2,2-trifluoroethyl)-3H-pyrrolo[2,3-d]pyrimidin-4(7H)-one.HCl

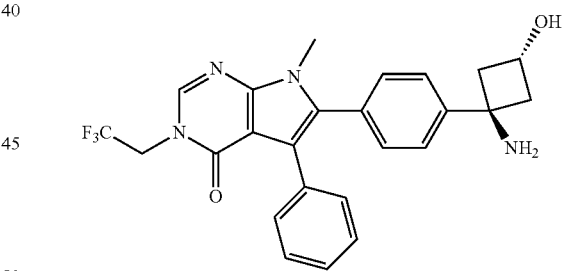

Step 1: 2-((1r,3r)-3-Hydroxy-1-(4-(7-methyl-4-oxo-5-phenyl-3-(2,2,2-trifluoroethyl)-4,7-dihydro-3H-pyrrolo[2,3-d]pyrimidin-6-yl)phenyl)cyclobutyl)isoindoline-1,3-dione To a solution of 6-bromo-7-methyl-5-phenyl-3-(2,2,2-trifluoroethyl)-3H-pyrrolo[2,3-d]pyrimidin-4(7H)-one (100 mg, 0.259 mmol), 2-((1r,3r)-3-hydroxy-1-(4-(4,4,5,5-tetramethyl-1,3,2-dioxaborolan-2-yl)phenyl)cyclobutyl)isoindoline-1,3-dione (130 mg, 0.311 mmol) and cesium carbonate (82 mg, 0.777 mmol) were added in 1,4-dioxane (5 ml) and water (1.25 ml). The reaction mixture was degassed by bubbling nitrogen through the reaction mixture for 5 min. 1,1'-Bis(diphenylphosphino)ferrocene-palladium(II)dichloride dichloromethane complex (42 mg, 0.05 mmol) was added, then the reaction was degassed with nitrogen for 5 min. The reaction mixture was stirred at 60° C. for 5 h under atmosphere of nitrogen. After allowing to cool to RT, the reaction mixture was concentrated in vacuo and the residue partitioned between water and ethyl acetate. The organic layer was washed with water (50 ml), brine (50 ml), dried ($Na_2SO_4$), filtered and concentrated in vacuo and the resulting residue was subjected to flash chromatography ($SiO_2$, gradient 0 to 50% ethyl acetate in cyclohexane) to afford the title compound (40 mg, 26%). LCMS $R_T$=1.38 min, M+H$^+$=599. $^1$H NMR (500 MHz, $CDCl_3$): δ 7.94 (1H, m), 7.75-7.82 (4H, m), 7.70-7.75 (2H, m), 7.25-7.30 (4H, m), 7.15-7.18 (3H, m), 4.67-4.74 (2H, m), 4.12-4.17 (1H, m), 3.66 (3H, s), 3.35-3.40 (2H, m), 3.10-3.17 (2H, m), 1.16 (3H, s).

Step 2: 6-(4-((1r,3r)-1-Amino-3-hydroxycyclobutyl)phenyl)-7-methyl-5-phenyl-3-(2,2,2-trifluoroethyl)-3H-pyrrolo[2,3-d]pyrimidin-4(7H)-one.HCl In a sealable tube was added 2-((1r,3r)-3-hydroxy-1-(4-(7-methyl-4-oxo-5-phenyl-3-(2,2,2-trifluoroethyl)-4,7-dihydro-3H-pyrrolo[2,3-a]pyrimidin-6-yl)phenyl)cyclobutyl)isoindoline-1,3-dione (40 mg, 0.067 mmol) and hydrazine hydrate (0.050 mL, 2.00 mmol) in methanol (0.5 ml) and water (0.5 ml). The tube was sealed and the reaction was heated at 120° C. for 30 min under microwave conditions (Biotage). The solvents were removed in vacuo. A SCX-2 silica cartridge was pre-treated with 20% v/v methanol in dichloromethane (100 ml). The residue was dissolved in dichloromethane (3×2 ml) and placed on to the SCX-2 column. The column was flushed with 20% v/v methanol in dichloromethane (100 ml) followed by 20% v/v 7M ammonia (in methanol) in dichloromethane (50 ml). The ammonia containing fraction was concentrated in vacuo and the resulting residue was purified by preparative HPLC. The pure fractions were concentrated and the resulting residue was dissolved in methanol (4 ml). A solution of HCl in methanol (5 μl of acetyl chloride added to 100 μl of methanol) was added. After 10 min, the solvents were removed in vacuo, the residue was dissolved in water (10 ml) and the solution was freeze-dried to afford the title compound (2 mg, 5%). LCMS $R_T$=0.85 min, M+H$^+$=469. $^1$H NMR (500 MHz, $CD_3OD$): δ 8.25 (1H, s), 7.54-7.58 (2H, m), 7.44-7.48 (2H, m), 7.24-7.27 (2H, m), 7.16-7.19 (3H, m), 3.71 (3H, s), 2.89 (2H, d), 2.70 (2H, d), 2.00 (3H, s), 1.25 (3H, s).

Example 12

6-(4-((1r,3r)-1-Amino-3-hydroxycyclobutyl)phenyl)-5-phenyl-3-(2,2,2-trifluoroethyl)thieno[2,3-d]pyrimidin-4(3H)-one.HCl Step 1: 2-((1r,3r)-3-Hydroxy-1-(4-(4-oxo-5-phenyl-3-(2,2,2-trifluoroethyl)-3,4-dihydrothieno[2,3-d]pyrimidin-6-yl)phenyl)cyclobutyl)isoindoline-1,3-dione To a solution of 6-bromo-5-phenyl-3-(2,2,2-trifluoroethyl)thieno[2,3-d]pyrimidin-4(3H)-one (100 mg, 0.257 mmol), 2-((1r,3r)-3-hydroxy-1-(4-(4,4,5,5-tetramethyl-1,3,2-dioxaborolan-2-yl)phenyl)cyclobutyl)isoindoline-1,3-dione (129 mg, 0.308 mmol) and caesium carbonate (250 mg, 0.777 mmol) were added in 1,4-dioxane (5 ml) and water (1.25 ml). The reaction mixture was degassed by bubbling nitrogen through the reaction mixture for 5 min. 1,1'-Bis(diphenylphosphino)ferrocene-palladium(II)dichloride dichloromethane complex (25 mg, 0.031 mmol) was added, then the reaction was degassed with nitrogen for 5 min. The reaction mixture was stirred at 60° C. for 5 h under an atmosphere of nitrogen. After allowing to cool to RT, the reaction mixture was concentrated in vacuo and the residue partitioned between water and ethyl acetate. The organic layer was washed with water (50 ml), brine (50 ml), dried ($Na_2SO_4$), filtered, concentrated in vacuo and the resulting residue was subjected to flash chromatography ($SiO_2$, gradient 0 to 50% ethyl acetate in cyclohexane) to afford the title compound (60 mg, 38%). LCMS $R_T$=1.41 min, M+H$^+$=602.

Step 2: 6-(4-((1r,3r)-1-Amino-3-hydroxycyclobutyl)phenyl)-5-phenyl-3-(2,2,2-trifluoroethyl)thieno[2,3-d]pyrimidin-4(3H)-one.HCl In a sealable tube 2-((1r,3r)-3-hydroxy-1-(4-(4-oxo-5-phenyl-3-(2,2,2-trifluoroethyl)-3,4-dihydrothieno[2,3-d]pyrimidin-6-yl)phenyl)cyclobutyl)isoindoline-1,3-dione (120 mg, 2 mmol) and hydrazine, $H_2O$ (970 μl, 2 mmol) were dissolved in methanol (2.5 ml) and water (2.5 ml) and the tube was sealed. The reaction was heated at 120° C. for 30 min under microwave conditions (Biotage). The solvent was removed in vacuo. A SCX-2 silica cartridge was pre-treated with 20% v/v methanol in dichloromethane (100 ml). The residue was dissolved in dichloromethane (3×2 ml) and placed on to the SCX-2 column. The column was flushed with 20% v/v methanol in dichloromethane (100 ml) followed by 20% v/v 4M ammonia (in methanol) in dichloromethane (50 ml). The ammonia containing fraction was reduced in vacuo. The residue was dissolved in methanol (4 ml). A solution of HCl in methanol (30 μl of acetyl chloride added to 0.5 ml of methanol) was added. After 10 min, the methanol was reduced in vacuo, the residue was dissolved in water (100 ml), and the resulting solution was filtered and freeze-dried to afford the title compound (45 mg, 45%). LCMS $R_T$=0.86 min, M+H$^+$=472. $^1$H NMR (500 MHz, $CD_3OD$): δ 8.40 (1H, s), 7.25-7.40 (9H, m), 4.90-4.95 (2H, m), 4.65-4.70 (1H, m), 2.97-3.03 (2H, m), 2.58-2.65 (2H, m).

Example 13

6-(4-((1r,3r)-1-Amino-3-hydroxy-3-methylcyclobutyl)phenyl)-5-(pyridin-4-yl)-3-(2,2,2-trifluoroethyl)furo[2,3-d]pyrimidin-4(3H)-one.TFA

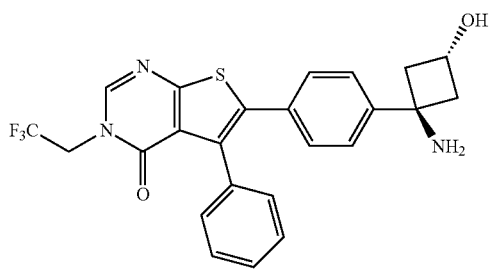 [SMILES: N[C@]1(c2ccc(-c3sc4ncn(CC(F)(F)F)c(=O)c4c3-c3ccccc3)cc2)C[C@@H](O)C1]

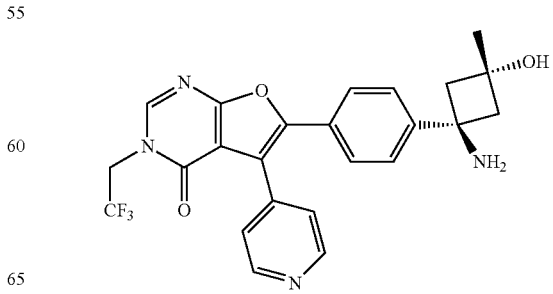

Step 1: 2-Iodofuran-3-carboxylic acid

To a stirring solution of furan-3-carboxylic acid (5 g, 44.6 mmol) in anhydrous tetrahydrofuran (200 ml) under a nitrogen atmosphere at −78° C. was added BuLi (44.6 ml, 112 mmol) dropwise. After stirring for 0.5 h, cooling was switched off and the mixture allowed to warm to room temperature. During warming, iodine (12.5 g, 49.1 mmol) as a solution in anhydrous tetrahydrofuran (30 ml) and added dropwise to the stirring mixture. Water was added (100 ml) and the organic solvents were removed in vacuo. The aqueous solution was acidified to ca pH 1 using 2M hydrochloric acid (aq) solution (ca 10-20 ml). The precipitated solid was collected by filtration and dried under vacuum and flowing nitrogen for 16 h to afford the title compound (6.21 g, 59%) that was used in the next step without further purification. LCMS $R_T$=0.78 min, M−H$^-$=236.8.

Step 2: 2-Iodofuran-3-carbonyl chloride

To 2-iodofuran-3-carboxylic acid (6.21 g, 26.1 mmol) was added thionyl chloride (20 ml, 274 mmol). The solution was heated while stirring to 70° C. for 5 h. The mixture was reduced in vacuo and the residue azeotroped with toluene (2×30 ml) to afford the crude title compound (6.69 g, 100%), which was used in the next step without further purification.

Step 3: 2-Iodo-N-(2,2,2-trifluoroethyl)furan-3-carboxamide

To a stirred solution of 2-iodofuran-3-carbonyl chloride (6.69 g, 26.1 mmol) in anhydrous tetrahydrofuran (120 ml) was added DIPEA (9.11 ml, 52.2 mmol) followed by 2,2,2-trifluoroethanamine (2.08 ml, 26.1 mmol) and the solution stirred for 1 h. The mixture was concentrated in vacuo. The residue was partitioned between 2M hydrochloric acid (aq) solution (100 ml) and dichloromethane (100 ml). The aqueous layer was separated and extracted with dichloromethane (2×100 ml). The combined organic layers were dried (phase separator) and concentrated in vacuo. The resulting residue was purified by silica gel chromatography (gradient 0-50% ethyl acetate in cyclohexane) to afford the title compound (4.38 g, 53%). LCMS $R_T$=0.98 min, M+H$^+$=319.9.

Step 4: 3-(2,2,2-Trifluoroethyl)furo[2,3-d]pyrimidin-4(3H)-one

Into seven 20 ml microwave tubes were placed 2-iodo-N-(2,2,2-trifluoroethyl)furan-3-carboxamide (0.62 g, 1.94 mmol), formimidamide, HCl (0.78 g, 9.72 mmol), copper(I) iodide (0.037 g, 0.194 mmol) and potassium carbonate (0.81 g, 5.83 mmol) in anhydrous DMF (13 ml). The tubes were sealed and heated to 100° C. for approximately 68 h with stirring. After cooling, the combined mixtures were partitioned between brine/water (1:1, 900 ml) and ethyl acetate (225 ml). The mixture was filtered through a plug of Celite. The aqueous phase was separated and extracted with ethyl acetate (3×225 ml). The combined organic layers were washed with brine/water (1:1, 4×225 ml), dried (anhydrous sodium sulfate), filtered and reduced in vacuo. The resulting residue was purified by silica gel chromatography (gradient 0-20% ethyl acetate in cyclohexane) to afford the title compound (647 mg, 22%). LCMS $R_T$=0.79 min, M+H$^+$=219.1.

Step 5: 6-Bromo-3-(2,2,2-trifluoroethyl)furo[2,3-d]pyrimidin-4(3H)-one

To a stirred solution of 3-(2,2,2-trifluoroethyl)furo[2,3-d]pyrimidin-4(3H)-one (0.64 g, 2.93 mmol) in anhydrous DMF (11 ml) at 0° C. was added bromine (0.333 ml, 6.45 mmol) and the mixture stirred for 30 min. The mixture was partitioned between ethyl acetate (30 ml) and an aqueous mixture (3:1:4, water, saturated sodium hydrogen carbonate solution and 20% w/w sodium thiosulfate solution, 110 ml). The aqueous phase was separated and extracted with ethyl acetate (3×30 ml). The combined ethyl acetate fractions were washed with brine/water (1:1, 4×30 ml), dried (anhydrous sodium sulfate), filtered and reduced in vacuo. The resulting residue was purified by silica gel chromatography (gradient 0-30% ethyl acetate in cyclohexane) to afford the title compound (673 mg, 77%). LCMS $R_T$=1.04 min, [M+H$^+$($^{79}$Br)]=297.0, [M+H$^+$($^{81}$Br)]=298.9.

Step 6: tert-Butyl ((1r,3l)-3-hydroxy-3-methyl-1-(4-(4-oxo-3-(2,2,2-trifluoroethyl)-3,4-dihydrofuro[2,3-d]pyrimidin-6-yl)phenyl)cyclobutyl)carbamate A stirring suspension of 6-bromo-3-(2,2,2-trifluoroethyl)furo[2,3-d]pyrimidin-4(3H)-one (50 mg, 0.168 mmol), tert-butyl ((1r,3r)-3-hydroxy-3-methyl-1-(4-(4,4,5,5-tetramethyl-1,3,2-dioxaborolan-2-yl)phenyl)cyclobutyl)carbamate (81 mg, 0.202 mmol) and sodium carbonate (53.5 mg, 0.505 mmol) in 1,4-dioxane (2 ml) and water (0.400 ml) was degassed with N$_2$ for 5 min. PdCl$_2$(dppf)-CH$_2$Cl$_2$adduct (13.8 mg, 0.017 mmol) was added and the reaction mixture degassed with N$_2$ for 5 min before heating to 70° C. for 40 h. Further PdCl$_2$(dppf)-CH$_2$Cl$_2$ adduct (13.8 mg, 0.017 mmol) was added and the reaction mixture degassed with N$_2$ for 5 min before heating to 70° C. for 1.5 h. The mixture was cooled and partitioned between saturated sodium hydrogen carbonate (5 ml) and DCM (5 ml). The layers were separated and the aqueous phase extracted with DCM (3×5 ml). The combined organic phases were dried (phase separator), filtered and concentrated in vacuo. The resulting residue was purified by silica gel chromatography (gradient 0-100% ethyl acetate in cyclohexane) to afford title compound which was used without further purification (41.5 mg, 50%). LCMS $R_T$=1.20 min, M-butene$^+$=438.1.

Step 7: tert-Butyl ((1r,3r)-1-(4-(5-bromo-4-oxo-3-(2,2,2-trifluoroethyl)-3,4-dihydrofuro[2,3-c]pyrimidin-6-yl)phenyl)-3-hydroxy-3-methylcyclobutyl)carbamate To a stirred solution of tert-butyl ((1 r,3r)-3-hydroxy-3-methyl-1-(4-(4-oxo-3-(2,2,2-trifluoroethyl)-3,4-dihydrofuro[2,3-d]pyrimidin-6-yl)phenyl)cyclobutyl)carbamate (41.5 mg, 0.084 mmol) in DMF (4 ml) was added NBS (74.8 mg, 0.420 mmol) and the solution heated to 80° C. for 10 min. The mixture was cooled and was partitioned between brine/water/ 20% w/w sodium thiosulfate solution (10:9:1, 40 ml) and ethyl acetate (10 ml). The layers were separated and the aqueous phase extracted with ethyl acetate (3×10 ml). The combined organic phases were dried (anhydrous sodium sulfate), filtered and concentrated in vacuo. The resulting residue was purified by silica gel chromatography (gradient 0-100% ethyl acetate in cyclohexane) to afford the title compound (13.6 mg, 28%). LCMS $R_T$=1.28 min, [M-Butene$^+$($^{79}$Br)]=516.0, [M-Butene$^+$($^{81}$Br)]=518.0. $^1$H NMR (500 MHz, CDCl$_3$) δ 8.04 (2H, d), 8.01 (1H, s), 7.52 (2H, d), (5.07 (1H, br s), 4.70 (2H, q), 2.51-2.78 (4H, m), 1.73 (1H, br s), 1.60 (3H, s), (1.40 (9H, br s).

Step 8: tert-Butyl ((1r,3r)-3-hydroxy-3-methyl-1-(4-(4-oxo-5-(pyridin-4-yl)-3-(2,2,2-trifluoroethyl)-3,4-dihydrofuro[2,3-d]pyrimidin-6-yl)phenyl)cyclobutyl)carbamate A stirred suspension of tert-butyl ((1r,3r)-1-(4-(5-bromo-4-oxo-3-(2,2,2-trifluoroethyl)-3,4-dihydrofuro[2,3-d]pyrimidin-6-yl)phenyl)-3-hydroxy-3-methylcyclobutyl)carbamate (13.6 mg, 0.024 mmol), pyridin-4-ylboronic acid (3.50 mg, 0.029 mmol) and sodium carbonate (7.56 mg, 0.071 mmol) in 1,4-dioxane (0.5 ml) and water (0.100 ml) was degassed with N₂ for 5 min. PdCl₂(dppf)-CH₂Cl₂ adduct (1.9 mg, 2.38 µmol) was added and the reaction mixture was degassed with N₂ for 5 min before heating to 70° C. and stirring for 21 h. Pyridin-4-ylboronic acid (3.50 mg, 0.029 mmol) and PdCl₂(dppf)-CH₂Cl₂ adduct (1.9 mg, 2.38 µmol) were added and the mixture was degassed with N₂ for 5 min before continuing to heat for 24 h. Pyridin-4-ylboronic acid (3.50 mg, 0.029 mmol) and PdCl₂(dppf)-CH₂Cl₂ adduct (1.9 mg, 2.38 µmol) were added and the mixture was degassed with N₂ for 5 min before continuing to heat for 4 h. After cooling, the mixture was partitioned between saturated sodium hydrogen carbonate (3 ml) and DCM (3 ml). The layers were separated and the aqueous phase extracted with DCM (3×3 ml). The combined organic phases were dried (phase separator), filtered and concentrated in vacuo. The resulting residue was purified by silica gel chromatography (gradient 0-100% ethyl acetate in cyclohexane then 0-10% methanol in ethyl acetate) to afford the title compound (4.6 mg, 34%). LCMS $R_T$=1.03 min, M+H⁺=571.2.

Step 9: 6-(4-((1r,3r)-1-Amino-3-hydroxy-3-methylcyclobutyl)phenyl)-5-(pyridin-4-yl)-3-(2,2,2-trifluoroethyl)furo[2,3-d]pyrimidin-4(3H)-one.TFA To a stirred solution of tert-butyl ((1r,3r)-3-hydroxy-3-methyl-1-(4-(4-oxo-5-(pyridin-4-yl)-3-(2,2,2-trifluoroethyl)-3,4-dihydrofuro[2,3-d]pyrimidin-6-yl)phenyl)cyclobutyl)carbamate (4.6 mg, 8.06 µmol) in anhydrous dichloromethane (1 ml) at 0° C. was added TFA (0.1 ml, 1.30 mmol) and the solution stirred for 30 min. The solution was concentrated in vacuo. The residue was twice azeotroped with dichloromethane (2 ml). The residue was dissolved in distilled water (2.5 ml) and freeze-dried to afford the title compound (3.5 mg, 62%). LCMS $R_T$=0.54 min, M+H⁺=471.1. ¹H NMR (500 MHz, CD₃OD) δ 8.68-8.76 (2H, m), 8.50 (1H, s), 7.81-7.87 (2H, m), 7.69 (2H, d), 7.64 (2H, d), 4.95 (2H, q), 2.90 (2H, d), 2.74 (2H, d), 1.52 (3H, s).

Example 14

6-(4-((1r,3r)-1-Amino-3-hydroxy-3-methylcyclobutyl)phenyl)-5-(pyridin-2-yl)-3-(2,2,2-trifluoroethyl)furo[2,3-d]pyrimidin-4(3H)-one.HCl

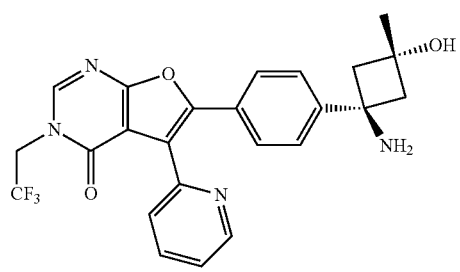 [SMILES: C[C@]1(O)C[C@@](N)(c2ccc(-c3oc4ncn(CC(F)(F)F)c(=O)c4c3-c3ccccn3)cc2)C1]

Step 1: tert-Butyl ((1r,3r)-3-hydroxy-3-methyl-1-(4-(4-oxo-5-(pyridin-2-yl)-3-(2,2,2-trifluoroethyl)-3,4-dihydrofuro[2,3-d]pyrimidin-6-yl)phenyl)cyclobutyl) carbamate A stirred solution of tert-butyl ((1r,3r)-1-(4-(5-bromo-4-oxo-3-(2,2,2-trifluoroethyl)-3,4-dihydrofuro[2,3-d]pyrimidin-6-yl)phenyl)-3-hydroxy-3-methylcyclobutyl)carbamate (165 mg, 0.288 mmol) and 2-(tributylstannyl)pyridine (0.114 ml, 0.317 mmol) in anhydrous toluene (3 ml) was degassed with N₂ for 5 min. Tetrakis(triphenylphosphine)palladium(0) (16.7 mg, 0.014 mmol) was added and the mixture heated to reflux under a nitrogen atmosphere for 6 h. After cooling, the reaction mixture was placed directly on to a silica column and purified by silica gel chromatography (gradient 0-100% ethyl acetate in cyclohexane; then 0-20% methanol in ethyl acetate) to afford the title compound (94.8 mg, 58%). LCMS $R_T$=1.14 min, M+H⁺=571.2. ¹H NMR (500 MHz, CDCl₃) b 8.70 (1H, d), 8.04 (1H, s), 7.79 (1H, td), 7.60 (1H, d), 7.52 (2H, d), 7.32-7.36 (3H, m), 4.94 (1H, br s), 4.67 (2H, q), 2.46-2.73 (4H, m), 1.68 (1H, br s), 1.57 (3H, s), 1.37 (9H, br s).

Step 2: 6-(4-((1r,3r)-1-Amino-3-hydroxy-3-methylcyclobutyl)phenyl)-5-(pyridin-2-yl)-3-(2,2,2-trifluoroethyl)furo[2,3-d]pyrimidin-4(3H)-one.HCl To a stirred solution of tert-butyl ((1r,3r)-3-hydroxy-3-methyl-1-(4-(4-oxo-5-(pyridin-2-yl)-3-(2,2,2-trifluoroethyl)-3,4-dihydrofuro[2,3-d]pyrimidin-6-yl)phenyl)cyclobutyl)carbamate (94.8 mg, 0.166 mmol) in anhydrous dichloromethane (2 ml) at 0° C. was added trifluoroacetic acid (1 ml, 13.0 mmol). After 60 min, the solution was reduced in vacuo. The residue was twice azeotroped with dichloromethane (2 ml). An SCX-2 silica cartridge (10 g) was pre-treated with 20% v/v methanol in dichloromethane (100 ml). The azeotroped residue was dissolved in dichloromethane (4×1 ml) and placed on to the SCX-2 column. After 1 h the column was flushed with 20% v/v methanol in dichloromethane (100 ml) followed by 20% v/v (7M ammonia in methanol) in dichloromethane (50 ml). The ammonia containing fraction was reduced in vacuo. The resulting residue was purified by preparative HPLC. The pure fractions were concentrated and the residue was dissolved in 1,4-dioxane (1 ml) and while stirring, a solution of HCl in methanol (35.4 µl of acetyl chloride added to 0.3 ml of methanol) was added. After 2 min, diethyl ether (20 ml) was added and the resulting suspension stirred for 5 min. The precipitate was collected by vacuum filtration under flowing nitrogen. The wet cake was washed with diethyl ether (2×4 ml), dissolved using water (4 ml), filtered, and freeze-dried to afford the title compound (40.0 mg, 44%). LCMS $R_T$=0.59 min, M+H⁺=471.1. ¹H NMR (500 MHz, CD₃OD) δ 9.00 (1H, d), 8.60 (1H, s), 8.59 (1H, td), 8.16 (1H, d), 8.10 (1H, t), 7.74 (4H, m), 5.01 (2H, q), 2.92 (2H, d), 2.79 (2H, d), 1.54 (3H, s).

Example 15

6-(4-((1r,3r)-1-Amino-3-hydroxy-3-methylcyclobutyl)phenyl)-7-methyl-5-(pyridin-2-yl)-3-(2,2,2-trifluoroethyl)-3H-pyrrolo[2,3-d]pyrimidin-4(7H)-one.TFA

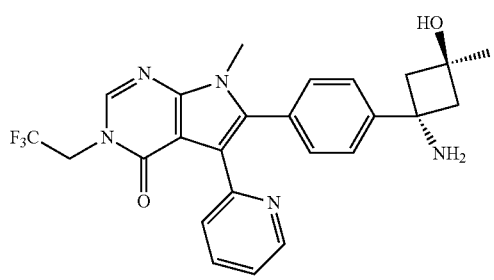 [SMILES: Cn1c(-c2ccc([C@]3(N)C[C@](C)(O)C3)cc2)c(-c2ccccn2)c2c(=O)n(CC(F)(F)F)cnc21]

Step 1: 4-Chloro-5-iodo-7-methyl-7H-pyrrolo[2,3-d]pyrimidine

To a stirred solution of 4-chloro-7H-pyrrolo[2,3-d]pyrimidine (2 g, 13.0 mmol) in anhydrous DMF (40 ml) was added potassium hydroxide (2.19 g, 39.1 mmol) followed by iodine (3.64 g, 14.3 mmol). The mixture was stirred for 1 h. Methyl iodide (0.814 ml, 13.0 mmol) was added and the mixture stirred for a further 1 h. The mixture was poured into 20% w/w sodium thiosulfate solution (400 ml). The formed solid was collected by filtration and dried under vacuum to afford the title compound which was used without further purification. LCMS $R_T$=1.12 min, $[M(^{35}Cl)+H]^+$=294.0, $[M(^{37}Cl)+H]^+$=295.9.

Step 2: 5-Iodo-7-methyl-3H-pyrrolo[2,3-d]pyrimidin-4(7H)-one

To a stirred solution of 4-chloro-5-iodo-7-methyl-7H-pyrrolo[2,3-d]pyrimidine (19.0 g, 64.9 mmol) in 1,4-dioxane (481 ml) was added 2M sodium hydroxide (aq) solution (479 ml, 959 mmol). The solution was heated to 100° C. and heated for 4 h. The solution was cooled. The organic solvent was removed in vacuo. The aqueous was acidified to ca pH 4 using concentrated hydrochloric acid. The resulting suspension was filtered and dried under vacuum and flowing nitrogen to afford the title compound which was used without further purification (15.7 g, 88%). LCMS $R_T$=0.65 min, $M+H^+$=276.0. $^1H$ NMR (500 MHz, $d_6$-DMSO) 11.93 (br s, 1H), 7.90 (s, 1H), 3.68 (s, 3H).

Step 3: 5-Iodo-7-methyl-3-(2,2,2-trifluoroethyl)-3H-pyrrolo[2,3-d]pyrimidin-4(7H)-one To a stirred suspension of 5-iodo-7-methyl-3H-pyrrolo[2,3-d]pyrimidin-4(7H)-one (13.7 g, 49.8 mmol) in anhydrous DMF (137 ml) was added potassium carbonate (13.8 g, 100 mmol) and 1,1,1-trifluoro-2-iodoethane (7.36 ml, 74.7 mmol). The resulting mixture was heated at 90° C. for 24 h. The reaction mixture was partitioned between brine/water (1:1, 1.41) and ethyl acetate (350 ml). The organic phase was separated and the aqueous phase was extracted with ethyl acetate (3×350 ml). The combined organic phase was washed with brine/water (1:1, 4×350 ml), dried and concentrated. The residue was purified by flash chromatography (0-45% ethyl acetate/cyclohexane) to give the title compound (13.7 g, 77%). LCMS $R_T$=1.05 min, $M+H^+$=358.0.

Step 4: 7-Methyl-5-(pyridin-2-yl)-3-(2,2,2-trifluoroethyl)-3H-pyrrolo[2,3-d]pyrimidin-4(7H)-one A mixture of 5-iodo-7-methyl-3-(2,2,2-trifluoroethyl)-3H-pyrrolo[2,3-d]pyrimidin-4(7H)-one (2 g, 5.60 mmol) and 2-(tributylstannyl)pyridine (2.2 ml, 6.79 mmol) in toluene (20 ml) was degassed. To the mixture was added tetrakis(triphenylphosphine)palladium(0) (0.324 g, 0.280 mmol). The resulting mixture was heated at 90° C. for 18 h. The reaction mixture was cooled and placed directly onto a silica column and purified by flash chromatography (0-100% ethyl acetate/cyclohexane) to give the title compound (0.37 g, 21%). LCMS RT=0.63 min, $M+H^+$=309.1

Step 5: 6-Bromo-7-methyl-5-(pyridin-2-yl)-3-(2,2,2-trifluoroethyl)-3H-pyrrolo[2,3-d]pyrimidin-4(7H)-one To a stirred solution of 7-methyl-5-(pyridin-2-yl)-3-(2,2,2-trifluoroethyl)-3H-pyrrolo[2,3-d]pyrimidin-4(7H)-one (53.6 mg, 0.174 mmol) in anhydrous DMF (1.8 ml) at 0° C. was added bromine (9.85 µl, 0.191 mmol) and the mixture stirred for 5 min. Further bromine (9.85 µl, 0.191 mmol) was added and the mixture stirred for 5 min. The mixture was partitioned between ethyl acetate (5 ml) and an aqueous mixture (3:1:4, water, saturated sodium hydrogen carbonate (aq) solution and 20% w/w sodium thiosulfate (aq) solution, 20 ml). The aqueous phase was separated and extracted with ethyl acetate (3×5 ml). The combined ethyl acetate fractions were washed with brine/water (1:1, 4×5 ml), dried (anhydrous sodium sulfate), filtered and reduced in vacuo. The resulting residue was purified by silica gel chromatography (0-5% methanol in ethyl acetate) to afford the title compound (46.8 mg, 70%). LCMS $R_T$=0.74 min, $[M+H^+(^{79}Br)]$=387.0, $[M+H^+(^{81}Br)]$=389.0.

Step 6: tert-Butyl ((1r,3r)-3-hydroxy-3-methyl-1-(4-(7-methyl-4-oxo-5-(pyridin-2-yl)-3-(2,2,2-trifluoroethyl)-4,7-dihydro-3H-pyrrolo[2,3-d]pyrimidin-6-yl)phenyl)cyclobutyl)carbamate A mixture of 6-bromo-7-methyl-5-(pyridin-2-yl)-3-(2,2,2-trifluoroethyl)-3H-pyrrolo[2,3-d]pyrimidin-4(7H)-one (80 mg, 0.207 mmol), tert-butyl ((1 r,3r)-3-hydroxy-3-methyl-1-(4-(4,4,5,5-tetramethyl-1,3,2-dioxaborolan-2-yl)phenyl)cyclobutyl)carbamate (100 mg, 0.248 mmol), sodium carbonate (65.7 mg, 0.620 mmol) and Pd(dppf)Cl$_2$.CH$_2$Cl$_2$ (17 mg, 0.021 mmol) in dioxane (6 ml) and water (1 ml) was degassed and heated at 70° C. for 3 h. After cooling, the organic phase was separated and concentrated. The residue was purified by flash chromatography (0-100% ethyl acetate/cyclohexane; then 0-10% methanol/ethyl acetate) to give the title compound (14 mg, 12%). LCMS $R_T$=0.97 min, $M+H^+$=584.2.

Step 7: 6-(4-((1r,3r)-1-Amino-3-hydroxy-3-methylcyclobutyl)phenyl)-7-methyl-5-(pyridin-2-yl)-3-(2,2,2-trifluoroethyl)-3H-pyrrolo[2,3-d]pyrimidin-4(7H)-one.TFA tert-Butyl ((1r,3r)-3-hydroxy-3-methyl-1-(4-(7-methyl-4-oxo-5-(pyridin-2-yl)-3-(2,2,2-trifluoroethyl)-4,7-dihydro-3H-pyrrolo[2,3-d]pyrimidin-6-yl)phenyl)cyclobutyl)carbamate (13 mg, 0.022 mmol) was dissolved in TFA (0.5 mL) and stirred for 30 seconds. The solution was then concentrated to dryness under reduced pressure. The residue was suspended in diethyl ether (2 mL) and concentrated to dryness under reduced pressure three times. The residue was then slurried in diethyl ether (2 mL) and after settling the supernatant solvent removed by pipette. This was repeated two times. The remaining solvent was removed under reduced pressure and dried to give the title compound (14 mg, 97%). LCMS $R_T$=0.49 min, $M+H^+$=484.2. $^1$H-NMR (500 MHz, CD$_3$OD) δ 8.74 (1H, m), 8.48 (1H, s), 8.05 (1H, m), 7.86 (2H, m), 7.66 (3H, m), 7.35 (1H, d), 5.08 (2H, q), 3.70 (3H, s), 2.98 (2H, d), 2.82 (2H, d), 1.56 (3H, s).

Example 16

6-(4-((1r,3r)-1-Amino-3-hydroxy-3-methylcyclobutyl)phenyl)-7-methyl-5-(pyridin-3-yl)-3-(2,2,2-trifluoroethyl)-3H-pyrrolo[2,3-d]pyrimidin-4(7H)-one.TFA

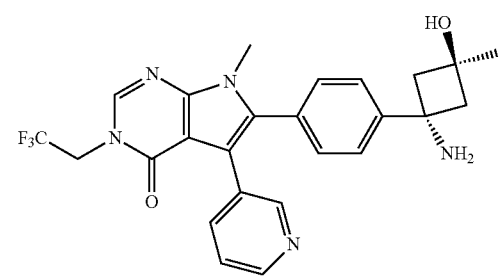 [SMILES: Cn1c(-c2ccc([C@]3(N)C[C@](C)(O)C3)cc2)c(-c2cccnc2)c2c(=O)n(CC(F)(F)F)cnc21]

Step 1: 7-Methyl-5-(pyridin-3-yl)-3-(2,2,2-trifluoroethyl)-3H-pyrrolo[2,3-d]pyrimidin-4(7H)-one A mixture of 5-iodo-7-methyl-3-(2,2,2-trifluoroethyl)-3H-pyrrolo[2,3-d]pyrimidin-4(7H)-one (358 mg, 1.00 mmol), pyridin-3-ylboronic acid (148 mg, 1.20 mmol), sodium carbonate (319 mg, 3.01 mmol) and PdCl$_2$(dppf)-CH$_2$Cl$_2$ adduct (82 mg, 0.100 mmol) in 1,4-dioxane (8 ml) and water (1.5 ml) was degassed. The resulting mixture was heated at 70° C. for 16 h. The reaction mixture was cooled down and partitioned between saturated sodium bicarbonate (35 mL) and DCM (35 mL). The organic phase was separated and concentrated in vacuo. The remaining residue was purified by flash chromatography (0-100% ethyl acetate/cyclohexane) to afford the title compound (280 mg, 90%). LCMS R$_T$=0.647 min, M+H$^+$=309.1

Step 2: 6-Bromo-7-methyl-5-(pyridin-3-yl)-3-(2,2,2-trifluoroethyl)-3H-pyrrolo[2,3-d]pyrimidin-4(7H)-one 7-methyl-5-(pyridin-3-yl)-3-(2,2,2-trifluoroethyl)-3H-pyrrolo[2,3-d]pyrimidin-4(7H)-one (0.28 g, 0.908 mmol) was dissolved in DMF (8 ml). The solution was cooled down to 0° C. Bromine (0.056 ml, 1.09 mmol) was added in dropwise. After 30 min, the reaction mixture was diluted with a aqueous mixture (3:1:4 water, saturated sodium bicarbonate solution and 20% w/w sodium thiosulfate solution, 80 ml) and extracted with ethyl acetate (3×50 ml). The combined organic phase was washed with water (4×60 ml), brine and concentrated to give title compound (0.13 g, 37%). LCMS R$_T$=0.81 min, [M+H$^+$($^{79}$Br)]=387.0, [M+H$^+$($^{81}$Br)]=389.0.

Step 3: tert-Butyl ((1r,3r)-3-hydroxy-3-methyl-1-(4-(7-methyl-4-oxo-5-(pyridin-3-yl)-3-(2,2,2-trifluoroethyl)-4,7-dihydro-3H-pyrrolo[2,3-d]pyrimidin-6-yl)phenyl)cyclobutyl)carbamate A mixture of 6-bromo-7-methyl-5-(pyridin-3-yl)-3-(2,2,2-trifluoroethyl)-3H-pyrrolo[2,3-d]pyrimidin-4(7H)-one (75 mg, 0.194 mmol), tert-butyl ((1 r,3r)-3-hydroxy-3-methyl-1-(4-(4,4,5,5-tetramethyl-1,3,2-dioxaborolan-2-yl)phenyl)cyclobutyl)carbamate (78 mg, 0.194 mmol), sodium carbonate (61.6 mg, 0.581 mmol) and PdCl$_2$(dppf)-CH$_2$Cl$_2$ adduct (15.8 mg, 0.019 mmol) in 1,4-dioxane (4 ml) and water (1 ml) was degassed. The mixture was heated at 70° C. for 3 h. The reaction mixture was cooled down and partitioned between water (50 ml) and DCM (50 ml). The organic phase was separated and concentrated. The residue was purified by flash chromatography (0-100% ethyl acetate/cyclohexane) to afford title compound (82 mg, 73%). LCMS R$_T$=1.0 min, M+H$^+$=584.2.

Step 4: 6-(4-((1r,3r)-1-Amino-3-hydroxy-3-methylcyclobutyl)phenyl)-7-methyl-5-(pyridin-3-yl)-3-(2,2,2-trifluoroethyl)-3H-pyrrolo[2,3-d]pyrimidin-4(7H)-one.TFA tert-Butyl ((1r,3r)-3-hydroxy-3-methyl-1-(4-(7-methyl-4-oxo-5-(pyridin-3-yl)-3-(2,2,2-trifluoroethyl)-4,7-dihydro-3H-pyrrolo[2,3-d]pyrimidin-6-yl)phenyl)cyclobutyl)carbamate (82 mg, 0.141 mmol) was dissolved in TFA (2 mL) and stirred for 30 seconds. The solution was concentrated to dryness under reduced pressure. The residue was dissolved in diethyl ether (2 mL) and concentrated to dryness under reduced pressure three times. The residue was then slurried in diethyl ether (2 mL) and after settling, the supernatant solvent was removed by pipette. This was repeated two times. The remaining solvent was removed under reduced pressure and dried to give the title compound (55 mg, 66%). LCMS R$_T$=0.52 min, M+H$^+$=484.1. $^1$H-NMR (500 MHz, CD$_3$OD) δ 8.63 (1H, m), 8.49 (1H, m), 8.33 (1H, s), 8.09 (1H, m), 7.71 (2H, d), 7.61 (1H, m), 7.55 (2H, d), 4.95 (2H, q), 3.74 (3H, s), 2.93 (2H, d), 2.77 (2H, d), 1.54 (3H, s).

Example 17

6-(4-((1r,3r)-1-Amino-3-hydroxy-3-methylcyclobutyl)phenyl)-7-methyl-5-(pyridin-4-yl)-3-(2,2,2-trifluoroethyl)-3H-pyrrolo[2,3-d]pyrimidin-4(7H)-one-.HCl

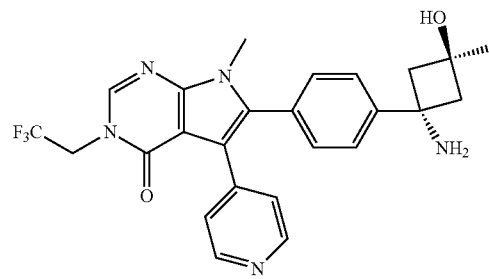 [SMILES: Cn1c(-c2ccc([C@]3(N)C[C@](C)(O)C3)cc2)c(-c2ccncc2)c2c(=O)n(CC(F)(F)F)cnc21]

Step 1: 7-Methyl-5-(pyridin-4-yl)-3-(2,2,2-trifluoroethyl)-3H-pyrrolo[2,3-d]pyrimidin-4(7H)-one A mixture of 5-iodo-7-methyl-3-(2,2,2-trifluoroethyl)-3H-pyrrolo[2,3-d]pyrimidin-4(7H)-one (358 mg, 1.00 mmol), pyridin-4-ylboronic acid (148 mg, 1.20 mmol), sodium carbonate (319 mg, 3.01 mmol) and PdCl$_2$(dppf)-CH$_2$Cl$_2$ adduct (82 mg, 0.100 mmol) in 1,4-dioxane (8 ml) and water (1.5 ml) was degassed. The resulting mixture was heated at 70° C. for 48 h. The reaction mixture was cooled and partitioned between saturated sodium bicarbonate solution (100 ml) and DCM (100 ml). The organic phase was separated and concentrated in vacuo. The remaining residue was purified by flash chromatography (0-100% ethyl acetate/cyclohexane) to afford the title compound (105 mg, 34%). LCMS R$_T$=0.64 min, M+H$^+$=309.1

Step 2: 6-Bromo-7-methyl-5-(pyridin-4-yl)-3-(2,2,2-trifluoroethyl)-3H-pyrrolo[2,3-d]pyrimidin-4(7H)-one A solution of 7-methyl-5-(pyridin-4-yl)-3-(2,2,2-trifluoroethyl)-3H-pyrrolo[2,3-d]pyrimidin-4(7H)-one (130 mg, 0.422 mmol) in DMF (6 ml) was cooled to 0° C. Bromine (0.026 ml, 0.506 mmol) was added dropwise. The resulting mixture was stirred at 0° C. for 60 min. The reaction mixture was partitioned between ethyl acetate (40 ml) and a mixture of aqueous (3:1:4, water, sodium bicarbonate solution and 20% w/w sodium thiosulfate solution, 40 ml). The organic phase was separated and washed with water (3×30 ml), brine and concentrated to give the title compound (160 mg, 98%). LCMS R$_T$=0.72 min, [M+H$^+$($^{79}$Br)]=387.0, [M+H$^+$($^{81}$Br)]=389.0.

Step 3: tert-Butyl ((1r,3r)-3-hydroxy-3-methyl-1-(4-(7-methyl-4-oxo-5-(pyridin-4-yl)-3-(2,2,2-trifluoroethyl)-4,7-dihydro-3H-pyrrolo[2,3-d]pyrimidin-6-yl)phenyl)cyclobutyl)carbamate A mixture of 6-bromo-7-methyl-5-(pyridin-4-yl)-3-(2,2,2-trifluoroethyl)-3H-pyrrolo[2,3-d]pyrimidin-4(7H)-one (160 mg, 0.413 mmol), tert-butyl ((1 r,3r)-3-hydroxy-3-methyl-1-(4-(4,4,5,5-tetramethyl-1,3,2-dioxaborolan-2-yl)phenyl)cyclobutyl)carbamate (200 mg, 0.496 mmol), sodium carbonate (131 mg, 1.24 mmol) and PdCl$_2$(dppf)-CH$_2$Cl$_2$ adduct (33.7 mg, 0.041 mmol) in 1,4-dioxane (8 ml) and water (1 ml) was degassed. The resulting mixture was heating at 70° C. for 3 h. The reaction mixture was partitioned between ethyl acetate (100 ml) and water (100 ml). The organic phase was separated and concentrated in vacuo. The remaining residue was purified by flash chromatography (0-100% ethyl acetate/cyclohexane) to give title compound (86 mg, 36%). LCMS R$_T$=0.96 min, M+H$^+$=584.2.

Step 4: 6-(4-((1 r,3r)-1-Amino-3-hydroxy-3-methylcyclobutyl)phenyl)-7-methyl-5-(pyridin-4-yl)-3-(2,2,2-trifluoroethyl)-3H-pyrrolo[2,3-d]pyrimidin-4(7H)-one.HCl tert-Butyl ((1r,3r)-3-hydroxy-3-methyl-1-(4-(7-methyl-4-oxo-5-(pyridin-4-yl)-3-(2,2,2-trifluoroethyl)-4,7-dihydro-3H-pyrrolo[2,3-d]pyrimidin-6-yl)phenyl)cyclobutyl)carbamate (85 mg, 0.146 mmol) was dissolved in 2,2,2-trifluoroacetic acid (4 ml, 51.9 mmol). The resulting solution was concentrated. The residue was partitioned between DCM (15 ml)/sodium bicarbonate solution (15 ml). The organic phase was separated and concentrated. The residue was purified by preparative HPLC. The pure fractions were combined, treated with HCl solution (2M in diethyl ether, 2 eq) and were concentrated in vacuo and freeze-dried to give the title compound (21 mg, 27%). LCMS R$_T$=0.50 min, M+H$^+$=484.2. $^1$H NMR (500 MHz, CD$_3$OD) δ 8.57 (2H, m), 8.41 (1H, s), 7.95 (2H, m), 7.80 (2H, d), 7.60 (2H, d), 4.96 (2H, q), 3.74 (3H, s), 4.95 (2H, q), 2.94 (2H, d), 2.80 (2H, d), 1.56 (3H, s).

Example 18

6-(4-((1 s,3s)-1-Amino-3-hydroxy-3-methylcyclobutyl)phenyl)-7-methyl-5-(pyridin-2-yl)-3-(2,2,2-trifluoroethyl)-3H-pyrrolo[2,3-d]pyrimidin-4(7H)-one.HCl

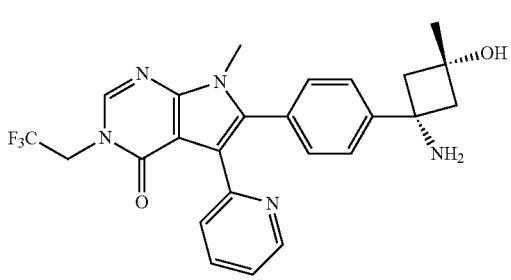

Step 1: tert-Butyl((1s,3s)-3-hydroxy-3-methyl-1-(4-(7-methyl-4-oxo-5-(pyridin-2-yl)-3-(2,2,2-trifluoroethyl)-4,7-dihydro-3H-pyrrolo[2,3-d]pyrimidin-6-yl)phenyl)cyclobutyl)carbamate A mixture of tert-butyl((1s,3s)-3-hydroxy-3-methyl-1-(4-(4,4,5,5-tetramethyl-1,3,2-dioxaborolan-2-yl)phenyl)cyclobutyl)carbamate (200 mg, 0.496 mmol), 6-bromo-7-methyl-5-(pyridin-2-yl)-3-(2,2,2-trifluoroethyl)-3H-pyrrolo[2,3-d]pyrimidin-4(7H)-one (160 mg, 0.413 mmol), Pd(dppf)Cl$_2$.CH$_2$Cl$_2$ (33.7 mg, 0.041 mmol) and sodium carbonate (131 mg, 1.24 mmol) in 1,4-dioxane (8 ml) and water (2 ml) was degassed and heated to 70° C. for 3 h. The organic phase was concentrated and purified by flash chromatography (0-100% ethyl acetate/cyclohexane; then 0-10% MeOH/DCM) to give the title compound (38 mg, 16%). LCMS R$_T$=0.94 min, M+H$^+$=584.2.

Step 2: 6-(4-((1s,3s)-1-Amino-3-hydroxy-3-methylcyclobutyl)phenyl)-7-methyl-5-(pyridin-2-yl)-3-(2,2,2-trifluoroethyl)-3H-pyrrolo[2,3-d]pyrimidin-4(7H)-one.HCl 2,2,2-trifluoroacetic acid (1 ml, 13.0 mmol) was added to tert-butyl((1s,3s)-3-hydroxy-3-methyl-1-(4-(7-methyl-4-oxo-5-(pyridin-2-yl)-3-(2,2,2-trifluoroethyl)-4,7-dihydro-3H-pyrrolo[2,3-d]pyrimidin-6-yl)phenyl)cyclobutyl)carbamate (38 mg, 0.065 mmol). The resulting solution was concentrated in vacuo. The residue was purified by flash chromatography (column was pretreated with 20% 7M NH$_3$ in MeOH/DCM; eluted with MeOH/DCM 0-20%) to give the product as the free base (9 mg). The material was dissolved in a mixture of MeOH (2 ml)/DCM (2 ml). 2M HCl in ether (2 eq) was added and the resulting solution was concentrated in vacuo to give the title compound (9.5 mg, 24%). LCMS R$_T$=0.57 min, M+H$^+$=484.2. $^1$H NMR (500 MHz, CD$_3$OD) δ 8.74 (1H, m), 8.49 (1H, s), 8.06 (1H, m), 7.78 (2H, m), 7.66 (3H, m), 7.35 (1H, d), 5.08 (2H, q), 3.69 (3H, s), 2.97 (2H, d), 2.76 (2H, d), 1.32 (3H, s).

Example 19

6-(4-((1s,3s)-1-Amino-3-hydroxy-3-methylcyclobutyl)phenyl)-5-(pyridin-2-yl)-3-(2,2,2-trifluoroethyl)thieno[2,3-d]pyrimidin-4(3H)-one.HCl

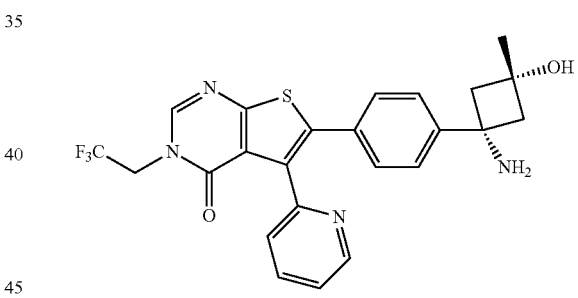

Step 1: 3-(2,2,2-Trifluoroethyl)thieno[2,3-d]pyrimidin-4(3H)-one

A mixture of thieno[2,3-d]pyrimidin-4(3H)-one (25 g, 164 mmol), 1,1,1-trifluoro-2-iodoethane (32.4 ml, 329 mmol) and cesium carbonate (53.5 g, 164 mmol) in DMF (100 ml) was heated at 100° C. for 18 h in a round bottom flask. 1 L of water was added to the reaction mixture and was extracted with ethyl acetate (3×300 ml). The combined organic phase was washed with water (500 ml), followed by brine. The organic phase was dried over MgSO$_4$, filtrated, then concentrated in vacuo. The residue was purified by flash chromatography (0-100% ethyl acetate/DCM) to obtain the title compound (27 g, 70%). LCMS R$_T$=0.88 min, M+H$^+$=235.1.

Step 2: 6-Bromo-3-(2,2,2-trifluoroethyl)thieno[2,3-d]pyrimidin-4(3H)-one

A solution of 3-(2,2,2-trifluoroethyl)thieno[2,3-d]pyrimidin-4(3H)-one (2 g, 8.54 mmol) and bromine (0.484 ml, 9.39 mmol) in DMF (20 ml) at 0° C. was stirred for 60 min. The reaction mixture was diluted with 1:1 sodium thiosulfate (25% aqueous solution)/saturated sodium bicarbonate (aq) solution (100 ml) and extracted with ethyl acetate (100 ml). The concentrated crude product was purified by flash chromatography (0-60% ethyl acetate/cyclohexane) to give the title compound (2.5 g, 94%). LCMS $R_T$=1.16 min, M+H+=312.9/314.9.

Step 3: tert-Butyl((1s,3s)-3-hydroxy-3-methyl-1-(4-(4-oxo-3-(2,2,2-trifluoroethyl)-3,4-dihydrothieno[2,3-d]pyrimidin-6-yl)phenyl)cyclobutyl)carbamate A mixture of 6-bromo-3-(2,2,2-trifluoroethyl)thieno[2,3-d]pyrimidin-4(3H)-one (1 g, 3.19 mmol), tert-butyl ((1s,3s)-3-hydroxy-3-methyl-1-(4-(4,4,5,5-tetramethyl-1,3,2-dioxaborolan-2-yl)phenyl)cyclobutyl)carbamate (1.29 g, 3.19 mmol), PdCl$_2$(dppf)-CH$_2$Cl$_2$ adduct (0.522 g, 0.639 mmol) and cesium carbonate (3.12 g, 9.58 mmol) in 1,4-dioxane (40 ml) and water (5 ml) was degassed and heated at 60° C. for 2 h. The reaction mixture was cooled down to room temperature. The organic phase was separated and concentrated to dryness. The residue was suspended with DCM (25 ml). The insoluble solid was filtered off under vacuum and washed using further DCM to give title compound (1.3 g, 80%). LCMS $R_T$=1.24 min, M+H+=510.

Step 4: tert-Butyl((1s,3s)-1-(4-(5-bromo-4-oxo-3-(2,2,2-trifluoroethyl)-3,4-dihydrothieno[2,3-d]pyrimidin-6-yl)phenyl)-3-hydroxy-3-methylcyclobutyl)carbamate A mixture of tert-butyl((1s,3s)-3-hydroxy-3-methyl-1-(4-(4-oxo-3-(2,2,2-trifluoroethyl)-3,4-dihydrothieno[2,3-d]pyrimidin-6-yl)phenyl)cyclobutyl)carbamate (1 g, 1.96 mmol) was suspended in DMF (45 ml). Bromine (0.121 ml, 2.36 mmol) was added dropwise. The resulting solution was stirred at room temperature for 50 min. The reaction mixture was diluted with 1:1 sodium thiosulfate (25% aqueous solution)/saturated sodium bicarbonate (aq) solution (200 ml) and extracted using ethyl acetate (2×150 ml). The combined organic phase was concentrated and purified by flash chromatography (0-70% ethyl acetate/cyclohexane) to give the title compound (0.35 g, 23%). LCMS $R_T$=1.30 min, M+H+=588/590.

Step 5: tert-Butyl((1s,3s)-3-hydroxy-3-methyl-1-(4-(4-oxo-5-(pyridin-2-yl)-3-(2,2,2-trifluoroethyl)-3,4-dihydrothieno[2,3-d]pyrimidin-6-yl)phenyl)cyclobutyl)carbamate A mixture of tert-butyl((1s,3s)-1-(4-(5-bromo-4-oxo-3-(2,2,2-trifluoroethyl)-3,4-dihydrothieno[2,3-d]pyrimidin-6-yl)phenyl)-3-hydroxy-3-methylcyclobutyl)carbamate (150 mg, 0.255 mmol), 2-(tributylstannyl)pyridine (113 mg, 0.306 mmol) and Pd(Ph$_3$P)$_4$ (29.5 mg, 0.025 mmol) in toluene (10 ml) was heated at 90° C. for 4 h. The reaction mixture was transferred directly onto a column and purified by flash chromatography (hexane; then 0-5% methanol/DCM) to give the title compound (60 mg, 40%). LCMS $R_T$=1.11 min, M+H+=587.1.

Step 6: 6-(4-((1s,3s)-1-Amino-3-hydroxy-3-methylcyclobutyl)phenyl)-5-(pyridin-2-yl)-3-(2,2,2-trifluoroethyl)thieno[2,3-d]pyrimidin-4(3H)-one.HCl tert-Butyl((1s,3s)-3-hydroxy-3-methyl-1-(4-(4-oxo-5-(pyridin-2-yl)-3-(2,2,2-trifluoroethyl)-3,4-dihydrothieno[2,3-d]pyrimidin-6-yl)phenyl)cyclobutyl)carbamate (24 mg, 0.041 mmol) was treated with trifluoroacetic acid (1 ml, 13.0 mmol). After 1 min, the TFA was removed in vacuo. The residue was purified by flash chromatography (column pretreated with 5% 7M methanol/DCM; eluted using 0-20% methanol/DCM) to afford the product as the free base, which was treated with 2M HCl in diethyl ether (4 eq), concentrated and freeze-dried to give the title compound (19 mg, 88%). LCMS $R_T$=0.697 min, M+H+=487.1. $^1$H NMR (500 MHz, CD$_3$OD) δ 8.91 (1H, m), 8.50 (1H, s), 8.42 (1H, m), 8.01 (1H, m), 7.85 (1H, m), 7.54 (2H, d), 7.44 (2H, d), 4.92 (2H, q), 2.85 (2H, d), 2.68 (2H, d), 1.24 (3H, s).

Example 20

6-(4-((1r,3r)-1-Amino-3-hydroxy-3-methylcyclobutyl)phenyl)-5-(pyridin-2-yl)-3-(2,2,2-trifluoroethyl)thieno[2,3-d]pyrimidin-4(3H)-one.HCl

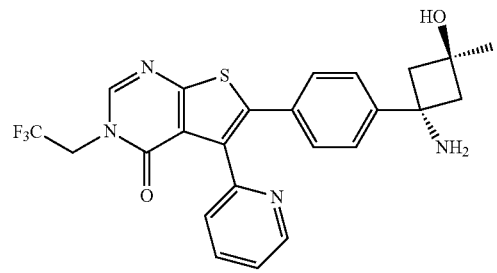 [SMILES: C[C@]1(O)C[C@@](N)(c2ccc(-c3sc4ncn(CC(F)(F)F)c(=O)c4c3-c3ccccn3)cc2)C1]

Step 1: tert-Butyl ((1r,3r)-3-hydroxy-3-methyl-1-(4-(4-oxo-3-(2,2,2-trifluoroethyl)-3,4-dihydrothieno[2,3-d]pyrimidin-6-yl)phenyl)cyclobutyl)carbamate To a solution of 6-bromo-3-(2,2,2-trifluoroethyl)thieno[2,3-d]pyrimidin-4(314)-one (1 g, 3.19 mmol), tert-butyl ((1r,3r)-3-hydroxy-3-methyl-1-(4-(4,4,5,5-tetramethyl-1,3,2-dioxaborolan-2-yl)phenyl)cyclobutyl)carbamate (1.55 g, 3.83 mmol) and cesium carbonate (3.12 g, 9.58 mmol) were added in 1,4-dioxane (20 ml) and water (5 ml). The reaction mixture was degassed under nitrogen for 5 min. Bis(diphenylphosphino)ferrocene-palladium(II)dichloride dichloromethane complex (0.522 g, 0.639 mmol) was added, then the reaction was degassed with nitrogen for 5 min. The reaction mixture was stirred at 60° C. for 1 h under nitrogen. After allowing to cool to RT the reaction mixture was concentrated in vacuo and the residue partitioned between water (60 ml) and ethyl acetate (60 ml). The organic layer was then washed with water (50 ml), brine (50 ml), dried (Na$_2$SO$_4$), filtered and concentrated in vacuo and the resulting residue was subjected to flash chromatography (SiO$_2$, gradient 0 to 70% ethyl acetate in dichloromethane) to afford the title compound (1.2 g, 74%). LCMS $R_T$=1.24 min, M+H+=510.

Step 2: tert-Butyl ((1r,3r)-1-(4-(5-bromo-4-oxo-3-(2,2,2-trifluoroethyl)-3,4-dihydrothieno[2,3-d]pyrimidin-6-yl)phenyl)-3-hydroxy-3-methylcyclobutyl)carbamate To a solution tert-butyl ((1r,3r)-3-hydroxy-3-methyl-1-(4-(4-oxo-3-(2,2,2-trifluoroethyl)-3,4-dihydrothieno[2,3-d]pyrimidin-6-yl)phenyl)cyclobutyl)carbamate (1.2 g, 2.35 mmol) in DMF, bromine (270 μl, 5.20 mmol) was added at RT. The reaction mixture was stirred at 50° C. for 18 h. After allowing to cool to RT, the reaction mixture was diluted with water (50 mL) and ethyl acetate was added (50 mL). The organic layer was washed with water (50 ml), brine (50 ml), dried ($Na_2SO_4$), filtered and concentrated in vacuo and the resulting residue was subjected to flash chromatography ($SiO_2$, gradient 0 to 50% ethyl acetate in dichloromethane) to afford the title compound (850 mg, 61%). LCMS $R_T$=1.31 min, M+H$^+$=588/590.

Step 3: tert-Butyl ((1r,3r)-3-hydroxy-3-methyl-1-(4-(4-oxo-5-(pyridin-2-yl)-3-(2,2,2-trifluoroethyl)-3,4-dihydrothieno[2,3-d]pyrimidin-6-yl)phenyl)cyclobutyl)carbamate A stirred solution of tert-butyl ((1r,3r)-1-(4-(5-bromo-4-oxo-3-(2,2,2-trifluoroethyl)-3,4-dihydrothieno[2,3-d]pyrimidin-6-yl)phenyl)-3-hydroxy-3-methylcyclobutyl)carbamate (100 mg, 0.170 mmol), 2-(tributylstannyl)pyridine (0.066 mL, 0.204 mmol) in anhydrous toluene (15 ml) was degassed with nitrogen for 5 min. Tetrakis(triphenylphosphine) palladium(0) (10 mg, 8 µmol) was added and the mixture heated to 110° C. for 5 h under nitrogen. After allowing to cool to RT the reaction mixture was diluted with water (50 ml) then ethyl acetate was added (50 ml). The organic layer was then washed with water (50 ml), brine (50 ml), dried ($Na_2SO_4$), filtered and concentrated in vacuo and the resulting residue was subjected to flash chromatography ($SiO_2$, gradient 0 to 50% ethyl acetate in dichloromethane) to afford the title compound (30 mg, 32%). LCMS $R_T$=1.11 min, M+H$^+$=587.

Step 4: 6-(4-((1 r,3r)-1-Amino-3-hydroxy-3-methylcyclobutyl)phenyl)-5-(pyridin-2-yl)-3-(2,2,2-trifluoroethyl)thieno[2,3-d]pyrimidin-4(3H)-one.HCl To a stirred solution of tert-butyl ((1r,3r)-3-hydroxy-3-methyl-1-(4-(4-oxo-3-(pyridin-2-yl)-5-(2,2,2-trifluoroethyl)-4,5-dihydrothieno[3,2-d]pyrimidin-2-yl)phenyl)cyclobutyl)carbamate (35 mg, 0.099 mmol) in DCM (1.5 ml), trifluoroacetic acid (1.5 mL) was added at 0° C. After 30 min, the solvents were removed in vacuo. A SCX-2 silica cartridge was pre-treated with 20% v/v methanol in dichloromethane (100 ml). The residue was dissolved in dichloromethane (3×2 ml) and placed on to the SCX-2 column. The column was flushed with 20% v/v methanol in dichloromethane (100 ml) followed by 20% v/v 4M ammonia (in methanol) in dichloromethane (50 ml). The ammonia containing fraction was reduced in vacuo. The residue was dissolved in methanol (4 ml). A solution of HCl in methanol (30 µL of acetyl chloride added to 500 µl of methanol) was added. After 10 min, the methanol was reduced in vacuo dissolved in water (100 ml), filtered and freeze-dried to afford the title compound as a white solid (20 mg, 69%). LCMS $R_T$=0.58 min, [M+H]$^+$=487. $^1$H NMR (500 MHz, d$_6$-DMSO): δ 8.60 (1H, d), 8.56 (1H, s), 8.45 (3H, bs), 7.84-7.89 (1H, m), 7.43-7.50 (4H, m), 7.30 (2H, d), 4.91 (2H, d), 2.60-2-62 (4H, m), 1.40 (3H, s).

AKT Kinase Assay Testing

Testing of the compounds was performed using an AKT Kinase Assay:

Activated AKT isoforms 1, 2 and 3 were assayed utilising a 5' FAM Crosstide (Seq. GRPRTSSFAEG-OH). The extent of kinase phosphorylation was determined by fluorescent polarisation using IMAP progressive binding reagent, which introduces binding beads which allow the reagent to specifically bind to phosphate residues via covalent co-ordination complex bonds.

iMAP binding solution stops Crosstide/kinase interaction and specifically binds phosphorylated substrates. The degree of phosphorylation is determined by fluorescent polarisation (excitation 485 nm; emission 528 nm) or the reduction in speed of rotation of the excited substrate.

The following materials were used in the assay:
a) Activated AKT isoforms (SignalChem.) dissolved in Complete Reaction buffer at a predetermined concentration selected so that the assay was carried out in the linear range.
b) AKT substrate peptide: FAM Crosstide (R7110) Molecular Devices, diluted in complete reaction buffer.
c) iMAP Progressive Screening Express Kit (R8127) Molecular Devices
d) Complete Reaction Buffer containing 0.1% BSA, 10 mM Tris-HCl, 10 mM $MgCl_2$, 0.05% $NaN_3$ and 0.01% phosphate free BSA, 1 mM DTT
e) Progressive Binding Solution containing 75% Buffer A, 25% Buffer B and low volume Binding Reagent which contains the binding entity for the assay
f) ATP diluted in complete reaction buffer
g) Black polystyrene 384 well assay plates (Nunc).
h) Biotek Synergy 4 Hybrid Plate reader.

5 µl of test compound was dissolved in DMSO (Sigma Aldrich) and serially diluted in complete reaction buffer to give a fourteen point half log dose response and plated into 384 well black plates. The compound was incubated at room temperature with activated AKT isoform (5 µl) at the predetermined concentration, for 45 min.

2.5 µl of ATP solution mixed with 2.5 µl of AKT substrate peptide (FAM Crosstide (R7110) Molecular Devices) were dispensed into each well and the plate centrifuged at 1000 rpm for 20 seconds to ensure homogenous mixing of reagents. The reaction mix was incubated in the dark for 1 h at room temperature.

The kinase reaction was stopped by the addition of Progressive Binding Solution and the mixture allowed to equilibrate for 1 h in the dark, at room temperature.

The fluorescent polarisation generated in each well was determined using a Biomek Synergy 4 Hybrid plate reader. In brief, each reaction solution was excited at 485 nm with the emission measured at 528 nm in both the parallel and perpendicular pathway.

The polarisation value generated in each well was calculated by Gen5 software (Biotek) and the % inhibition of kinase activity compared to vehicle control was calculated via GraphPad Prism. $IC_{50}$ values for each compound were calculated by non-linear regression analysis using Prism software.

All plates were internally controlled by two methods. Firstly, by calculating the signal:noise ratio; based on kinase polarisation without inhibitor and polarisation generated by complete reaction buffer in the absence of activated kinase. Secondly by determining $IC_{50}$ values generated by known inhibitors of the AKT isoforms.

The data was analysed using GraphPad Prism, with $IC_{50}$ values generated using non-linear regression of the data set.

Analysis of Compound Effects on AKT Signalling Pathways: Inhibition of pAKT in PC3 Cells PC3 cells were seeded overnight in 96 well plates followed by serum starvation for 4 h. Increasing concentrations of AKT inhibitor, in complete medium (RPMI 1640), were added to the cells and incubated for a further 24 h.

The cells were fixed in paraformaldehyde, permeabilised and blocked in BSA, followed by incubation with pAKT (Ser473) and total AKT antibody overnight (R&D Systems). Secondary antibody mixture was added, followed by a combination of fluorescent substrates added for a final incubation.

Fluorescent intensities for each antibody were read at 540/600 nm and 360/450 nm respectively on a Synergy 4 μlate reader. The percentage change in fluorescent intensity was plotted against log concentration of inhibitor; to generate $IC_{50}$ values (GraphPad Prism).

Testing of Comparative Examples

The compounds represented in the table immediately below are compounds synthesised by the Inventors. Compounds A, F, and L are compounds within the main structural formula as set out in WO2011/055115, but which lack the hydroxy-substituted cyclobutane ring which is present in the compounds of the present invention. Compound A is Example 106 from that International Application and compounds F and L are covered by the formula in WO2011/055115 but not specifically mentioned in the Examples of that specification. The remainder of the compounds are compounds according to the present invention and show derivitisation at the cyclobutane ring in accordance with the present invention.

Compound A

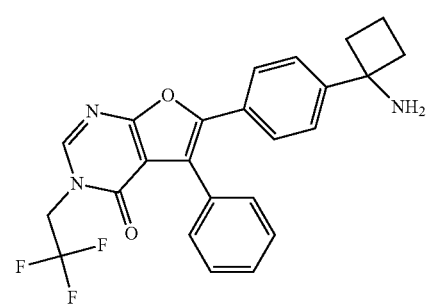

$C_{24}H_{20}F_3N_3O_2$

Compound 2

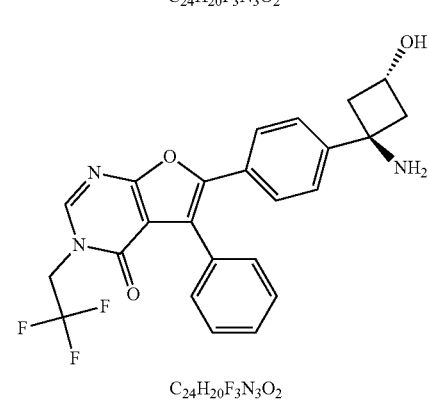

$C_{24}H_{20}F_3N_3O_2$

Compound 4

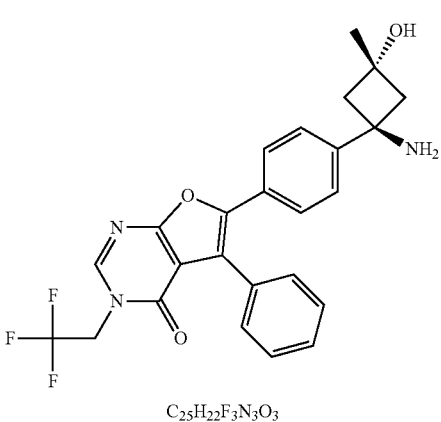

$C_{25}H_{22}F_3N_3O_3$

-continued

Compound 3

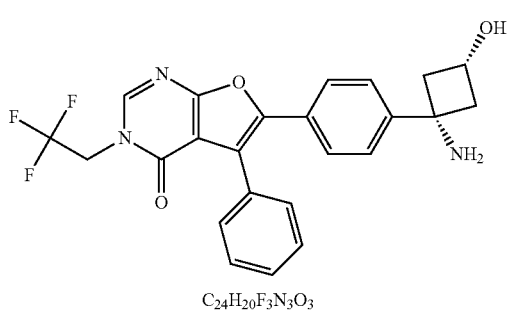

$C_{24}H_{20}F_3N_3O_3$

Compound 1

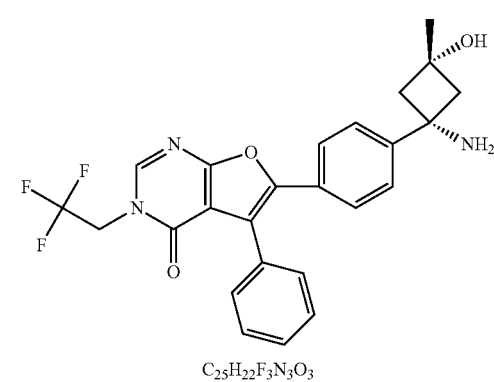

$C_{25}H_{22}F_3N_3O_3$

Compound F

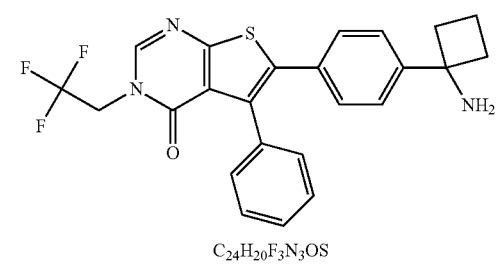

$C_{24}H_{20}F_3N_3OS$

Compound 5

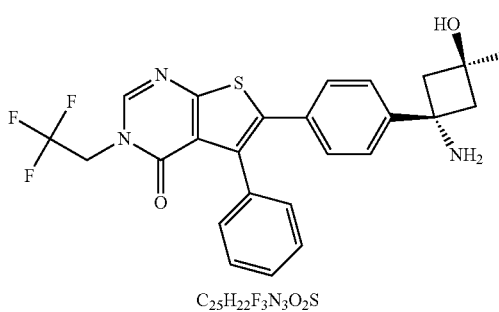

$C_{25}H_{22}F_3N_3O_2S$

Compound 8

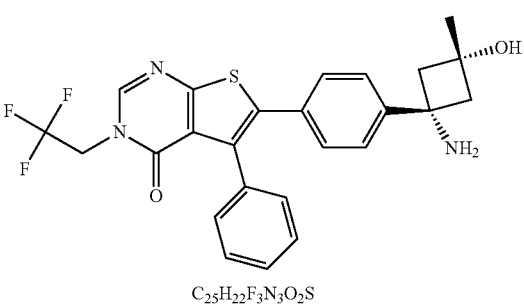

$C_{25}H_{22}F_3N_3O_2S$

Compound 9
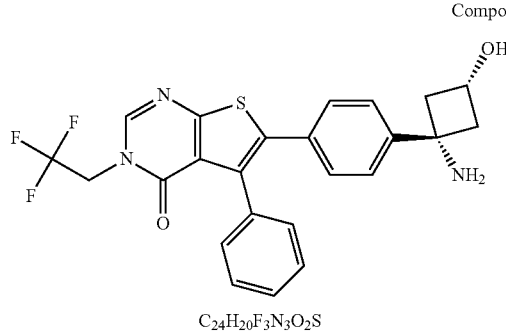
C₂₄H₂₀F₃N₃O₂S
Compound 6
C₂₆H₂₅F₃N₄O₂
Compound 7
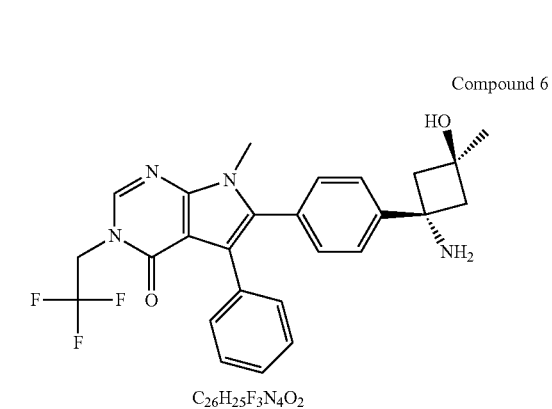
C₂₅H₂₃F₃N₄O₂
Compound L
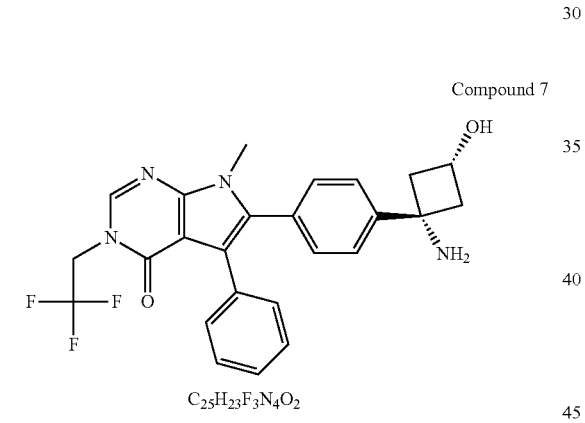
C₂₅H₂₃F₃N₄O
Compound 10
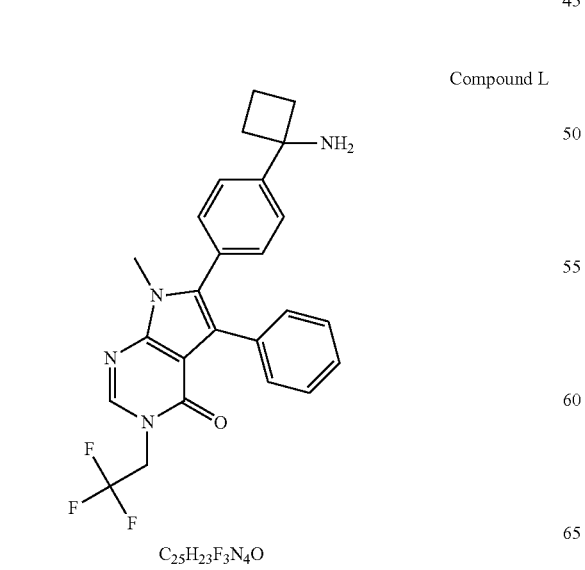
C₂₆H₂₅F₃N₄O₂
Compound 11
C₂₅H₂₃F₃N₄O₂
Compound 12
C₂₄H₂₀F₃N₃O₂S
Compound 13
C₂₄H₂₁F₃N₄O₃
Compound 14
C₂₄H₂₁F₃N₄O₃

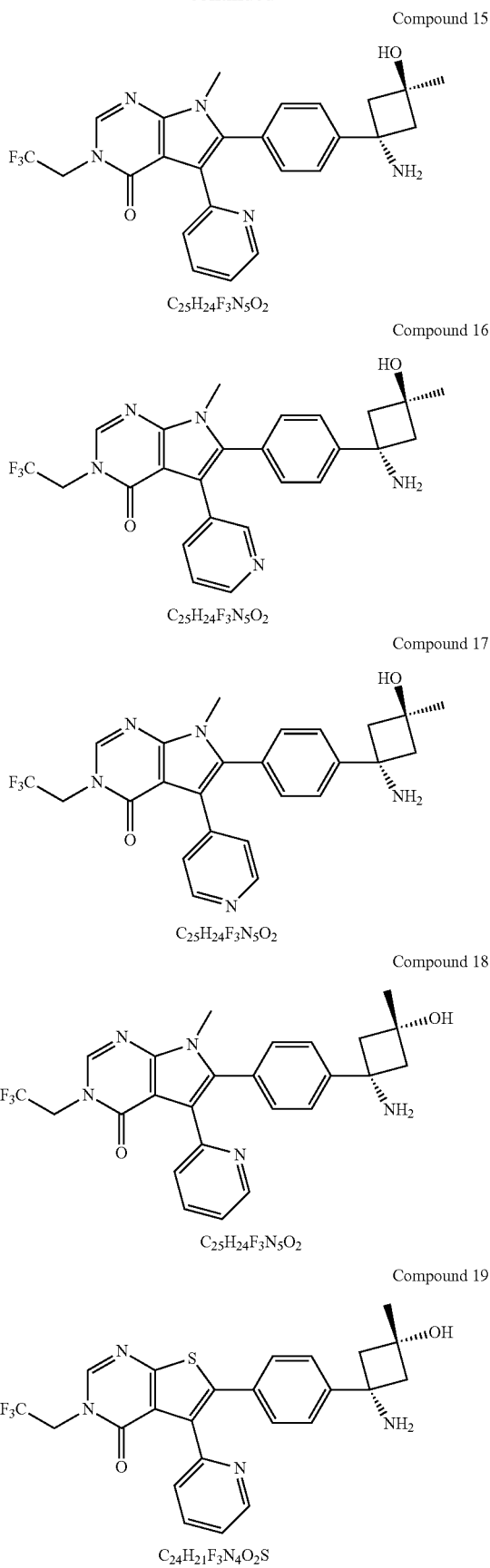

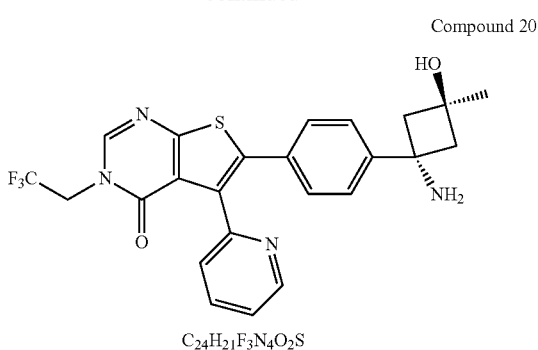

Surprisingly, the incorporation of hydroxy-substitution on the cyclobutane ring of compounds covered by the present invention conveys unexpected advantages relative to their non-hydroxylated counterparts. A discussion of the advantages associated with derivitisation of the cyclobutane ring in accordance with the present invention follows the experimental data below:

TABLE I

| Compound | AKT1 IC$_{50}$ | AKT2 IC$_{50}$ | AKT3 IC$_{50}$ |
|---|---|---|---|
| A | * | ** | * |
| 2 | * | *** | * |
| 4 | *** | *** | *** |
| 3 | ** | *** | ** |
| 1 | ** | *** | ** |
| F | ** | * | * |
| 5 | *** | ** | ** |
| 8 | *** | ** | ** |
| 9 | *** | *** | ** |
| 6 | *** | *** | ** |
| 7 | ** | *** | ** |
| L | ** | ** | * |
| 10 | ** | *** | ** |
| 11 | * | ** | * |
| 12 | ** | ** | ** |
| 13 | * | *** | * |
| 14 | * | * | * |
| 15 | * | * | * |
| 16 | * | * | * |
| 17 | * | * | * |
| 18 | * | * | * |
| 19 | * | * | * |
| 20 | * | * | * |

* IC$_{50}$ ≤ 300 nM  * IC$_{50}$ ≤ 20 nM  *** IC$_{50}$ ≤ 1 μM
 300 nM < IC$_{50}$ ≤ 1.5 μM    20 nM < IC$_{50}$ ≤ 100 nM   ** 1 μM < IC$_{50}$ ≤ 6 μM
* IC$_{50}$ > 1-5 μM   * IC$_{50}$ > 100 nM   * IC$_{50}$ > 6 μM

TABLE II

| Compound | >=80% in Selectscreen (at 10 uM) other than AKT1 | Fraction unbound (human plasma) % | T½ (rat) h |
|---|---|---|---|
| A | * | * | * |
| 4 | ** | — | — |
| 1 | * | *** | *** |

TABLE II-continued

| Compound | >=80% in Selectscreen (at 10 uM) other than AKT1 | Fraction unbound (human plasma) % | T½ (rat) h |
|---|---|---|---|
| 5 | ** | ** | *** |
| 6 | *** | ** | *** |
| | *** 0 kinases | *** Fu ≥ 5 | *** T½ ≤ 10 h |
| | ** 1-2 kinases | ** 2 < Fu < 5 | ** 10 h < T½ ≤ 24 h |
| | * >2 kinases | * Fu ≤ 2 | * >24 h |
| | "—" not determined | "—" not determined | "—" not determined |

As already mentioned, Compounds A, F, and L are compounds within the main structural formula as sent out in WO2011/055115. Compound A represents a furan derivative, Compound F is a thiophene derivative and Compound L is a pyrrole. The differences between the compounds of WO2011/055115 and those of the present invention reside in the specific substitution of the cyclobutane ring in compounds of the present invention.

Compound 2 is a trans hydroxyaminocyclobutanyl derivative related to compound A showing improved potency against AKT2 when compared with compound A.

Compound 4 is similar to compound 2 with the exception that it has methyl substitution at the same position as the hydroxyl position. Compound 4 also has the polar groups in a trans orientation and shows improved potency against all of the AKT isoforms and less off-target kinase activity in the SelectScreen® panel when compared with Compound A.

Compound 3 is similar to compound 2 in that it is a hydroxyaminocyclobutanyl derivative related to compound A, this time with the polar groups in a cis configuration. Compound 3 also shows improved potency against all AKT isoforms when compared with Compound A.

Compound 1 is an isomer of compound 4 but has the two polar groups in a cis configuration. This compound shows improved potency against all AKT isoforms when compared with Compound A. It also shows a significantly higher unbound fraction (human plasma) than that found for Compound A and a shorter T1/2 in rodent, which is predicted to lead to a half life more suitable for qd/bid dosing in higher species.

Compound 5 is similar to Compound F but has hydroxyl and methyl substitution at the cyclobutane ring. The polar groups of Compound 5 are in a trans orientation. Compound 5 shows improved potency against all AKT isoforms when compared to Compound F. It also shows a significantly higher unbound fraction (human plasma) than that found for Compound A and a shorter T1/2 in rodent, which is predicted to lead to a half life more suitable for qd/bid dosing in higher species Compound 8 is an isomer of compound 5 with the orientation of the polar groups being in a cis configuration. Compound 8 also demonstrates improved potency against all AKT isoforms when compared with compound F.

Compound 9 has the polar groups in a cis configuration as in Compound 8 but the methyl substitution is absent. Compound 9 shows improved potency against all AKT isoforms when compared with compound F.

Compound 6 is a methylhydroxyaminocyclobutanyl derivative related to compound L. In Compound 6 the polar groups are in a trans configuration. Compound 6 shows improved potency against all AKT isoforms when compared with compound L. It also shows a significantly higher unbound fraction (human plasma) than that found for Compound A and a shorter T1/2 in rodent, which is predicted to lead to a half life more suitable for qd/bid dosing in higher species Compound 7 is a cis hydroxyaminocyclobutanyl derivative related to compound L. Compound 7 shows improved potency against all AKT isoforms when compared with compound L.

Compound 10 is a methylhydroxyaminocyclobutanyl derivative related to compound L with the polar groups in a cis configuration. Compound 10 shows improved potency against AKT2 and AKT3 when compared to compound L.

Compound 11 is a trans hydroxyaminocyclobutanyl derivative related to compound L.

Compound 12 is a trans hydroxyaminocyclobutanyl derivative related to compound F. Compound 12 shows improved potency against AKT2 and AKT3 when compared to compound F.

Compound 13 is a methylhydroxyaminocyclobutanyl derivative related to compound A with the polar groups in a trans configuration. Compound 13 has Ar=4-pyridine compared to Ar=phenyl when compared to compound A. Compound 13 shows improved potency against AKT2 and greater selectivity for AKT2 over AKT1 and AKT3 when compared to compound A.

Compound 14 is a methylhydroxyaminocyclobutanyl derivative related to compound A with the polar groups in a trans configuration. Compound 14 has Ar=2-pyridine compared to Ar=phenyl when compared to compound A.

Compound 15 is a methylhydroxyaminocyclobutanyl derivative related to compound L with the polar groups in a trans configuration. Compound 15 has Ar=2-pyridine compared to Ar=phenyl when compared to compound L.

Compound 16 is a methylhydroxyaminocyclobutanyl derivative related to compound L with the polar groups in a trans configuration. Compound 16 has Ar=3-pyridine compared to Ar=phenyl when compared to compound L.

Compound 17 is a methylhydroxyaminocyclobutanyl derivative related to compound L with the polar groups in a trans configuration. Compound 17 has Ar=4-pyridine compared to Ar=phenyl when compared to compound L.

Compound 18 is a methylhydroxyaminocyclobutanyl derivative related to compound L with the polar groups in a cis configuration. Compound 18 has Ar=2-pyridine compared to Ar=phenyl when compared to compound L.

Compound 19 is a methylhydroxyaminocyclobutanyl derivative related to compound F with the polar groups in a cis configuration. Compound 19 has Ar=2-pyridine compared to Ar=phenyl when compared to compound F.

Compound 20 is a methylhydroxyaminocyclobutanyl derivative related to compound F with the polar groups in a trans configuration. Compound 20 has Ar=2-pyridine compared to Ar=phenyl when compared to compound F.

The inventors have surprisingly found that hydroxy-substitution of the cyclobutane ring distal to the amino group of the known compounds gives the advantageous effects presented herein. Furthermore, adding small alkyl groups and altering the orientation of the bonding at the cyclobutane ring to give both cis and trans forms of the compounds has shown that other advantageous properties are available from these compounds.

Compounds of the invention show improved potency against various isoforms of AKT. As can be seen from the comparative data presented above, the compounds of the invention also have a number of other advantages to offer.

For ease of reference note that the compounds above are numbered according to the Examples in which they are prepared.

The invention claimed is:
1. A compound according to Formula (I):

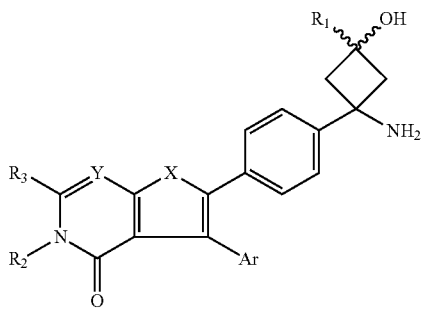

wherein:
Y is selected from N, and CR, where R is hydrogen, Z, cyano, or CONR'R" where R' and R" are independently H or Z;
X is O, NR'" or S where R'" is hydrogen or Z;
Ar is aryl or heteroaryl;
$R^1$ is hydrogen or Z;
$R^2$ is Z;
$R^3$ is hydrogen, Z, or $NR^4R^5$ where $R^4$ and $R^5$ are independently H or Z;
wherein Z is a saturated or unsaturated alkyl group containing 1 to 6 carbon atoms; wherein the alkyl group may be unsubstituted or substituted with one or more groups selected from CN, $CO_2H$, $CONH_2$, CONHR, $CONR^aR^b$, $CO_2R$, $NH_2$, NHR, $NR^aR^b$, OH, OR, SH, SR, F, Cl, Br and I, wherein each R, $R^a$ and $R^b$ is independently alkyl or aryl group attached to the oxygen, nitrogen or sulfur atom through a carbon atom of each group; or wherein $R^a$ and $R^b$ form a heterocycle together with the heteroatom to which they are attached; wherein if more than one substituent is present, the substituents are independently selected from one another unless they form a part of an amide group; wherein any substituents may in turn be substituted with further carbon-containing groups;
or a pharmaceutically acceptable salt, stereoisomer or tautomer thereof.
2. The compound of claim 1, wherein X is O or S.
3. The compound of claim 2, wherein X is O.
4. The compound of claim 1, wherein X is S or N—$CH_3$.
5. The compound of claim 1, wherein Y is nitrogen.
6. The compound of claim 1, wherein $R^3$ is hydrogen.
7. The compound of claim 1, wherein $R^2$ is halo substituted Z.
8. The compound of claim 7, wherein $R^2$ is fluoro substituted Z.
9. The compound of claim 8, wherein $R^2$ is 2,2,2 trifluoroethyl.
10. The compound of claim 1, wherein Ar is a nitrogen containing heteroaryl moiety.
11. The compound of claim 1, wherein Ar is phenyl, 2-pyridyl, 3-pyridyl, 4-pyridyl or thiophene.
12. The compound of claim 11, wherein Ar is phenyl.
13. The compound of claim 1, wherein $R^1$ is methyl.
14. The compound of claim 1, wherein the hydroxyl group bound to the cyclobutane moiety is trans with respect to the amine group also bound to the cyclobutane moiety.
15. The compound of claim 1, wherein the hydroxyl group bound to the cyclobutane moiety is cis with respect to the amine group also bound to the cyclobutane moiety.
16. The compound of claim 1, wherein
Z is selected from lower alkyl, lower heteroalkyl, lower cycloalkyl, lower cycloheteroalkyl, lower alkenyl, lower alkynyl, lower heteroalkenyl, lower heteroalkynyl, lower cycloalkenyl and lower cyclo-heteroalkenyl.
17. The compound of claim 1, wherein the compound is being selected from the group consisting of:
6-(4-((1 s,3 s)-1-amino-3-hydroxy-3-methylcyclobutyl)phenyl)-5-phenyl-3-(2,2,2-trifluoroethyl)furo[2,3-d]pyrimidin-4(3H)-one;
6-(4-((1r,3r)-1-amino-3-hydroxycyclobutyl)phenyl)-5-phenyl-3-(2,2,2-trifluoroethyl)furo[2,3-4 pyrimidin-4(3H)-one;
6-(4-((1 s,3 s)-1-amino-3-hydroxycyclobutyl)phenyl)-5-phenyl-3-(2,2,2-trifluoroethyl)furo[2,3-d]pyrimidin-4(3H)-one;
6-(4-((1r,3r)-1-amino-3-hydroxy-3-methylcyclobutyl)phenyl)-5-phenyl-3-(2,2,2-trifluoroethyl)furo[2,3-d]pyrimidin-4(3H)-one;
6-(4-((1r,3r)-1-amino-3-hydroxy-3-methylcyclobutyl)phenyl)-5-phenyl-3-(2,2,2-trifluoroethyl)thieno[2,3-d]pyrimidin-4(3H)-one;
6-(4-((1r,3r)-1-amino-3-hydroxy-3-methylcyclobutyl)phenyl)-7-methyl-5-phenyl-3-(2,2,2-trifluoroethyl)-3H-pyrrolo[2,3-d]pyrimidin-4(7H)-one;
6-(4-((1 s,3 s)-1-amino-3-hydroxycyclobutyl)phenyl)-7-methyl-5-phenyl-3-(2,2,2-trifluoroethyl)-3H-pyrrolo[2,3-d]pyrimidin-4(7H)-one;
6-(4-((1s,3s)-1-amino-3-hydroxy-3-methylcyclobutyl)phenyl)-5-phenyl-3-(2,2,2-trifluoroethyl)thieno[2,3-d]pyrimidin-4(3H)-one; and
6-(4-((1s,3s)-1-amino-3-hydroxycyclobutyl)phenyl)-5-phenyl-3-(2,2,2-trifluoroethyl)thieno[2,3-4 pyrimidin-4(3H)-one;
6-(4-((1s,3s)-1-amino-3-hydroxy-3-methylcyclobutyl)phenyl)-7-methyl-5-phenyl-3-(2,2,2-trifluoroethyl)-3H-pyrrolo[2,3-d]pyrimidin-4(7H)-one;
6-(4-((1r,3r)-1-amino-3-hydroxycyclobutyl)phenyl)-7-methyl-5-phenyl-3-(2,2,2-trifluoroethyl)-3H-pyrrolo[2,3-d]pyrimidin-4(7H)-one;
6-(4-((1r,3r)-1-amino-3-hydroxycyclobutyl)phenyl)-5-phenyl-3-(2,2,2-trifluoroethyl)thieno[2,3-4 pyrimidin-4(3H)-one;
6-(4-((1r,3r)-1-amino-3-hydroxy-3-methylcyclobutyl)phenyl)-5-(pyridin-4-yl)-3-(2,2,2-trifluoroethyl)furo[2,3-d]pyrimidin-4(3H)-one;
6-(4-((1r,3r)-1-amino-3-hydroxy-3-methylcyclobutyl)phenyl)-5-(pyridin-2-yl)-3-(2,2,2-trifluoroethyl)furo[2,3-d]pyrimidin-4(3H)-one;
6-(4-((1r,3r)-1-amino-3-hydroxy-3-methylcyclobutyl)phenyl)-7-methyl-5-(pyridin-2-yl)-3-(2,2,2-trifluoroethyl)-3H-pyrrolo[2,3-d]pyrimidin-4(7H)-one;
6-(4-((1r,3r)-1-amino-3-hydroxy-3-methylcyclobutyl)phenyl)-7-methyl-5-(pyridin-3-yl)-3-(2,2,2-trifluoroethyl)-3H-pyrrolo[2,3-d]pyrimidin-4(7H)-one;
6-(4-((1r,3r)-1-amino-3-hydroxy-3-methylcyclobutyl)phenyl)-7-methyl-5-(pyridin-4-yl)-3-(2,2,2-trifluoroethyl)-3H-pyrrolo[2,3-d]pyrimidin-4(7H)-one;
6-(4-((1s,3s)-1-amino-3-hydroxy-3-methylcyclobutyl)phenyl)-7-methyl-5-(pyridin-2-yl)-3-(2,2,2-trifluoroethyl)-3H-pyrrolo[2,3-d]pyrimidin-4(7H)-one;
6-(4-((1s,3s)-1-amino-3-hydroxy-3-methylcyclobutyl)phenyl)-5-(pyridin-2-yl)-3-(2,2,2-trifluoroethyl)thieno[2,3-d]pyrimidin-4(3H)-one;

6-(4-((1r,3r)-1-amino-3-hydroxy-3-methylcyclobutyl)phenyl)-5-(pyridin-2-yl)-3-(2,2,2-trifluoroethyl)thieno[2,3-d]pyrimidin-4(3H)-one;

or a pharmaceutically acceptable salt, stereoisomers and tautomer thereof.

18. The compound of claim 1, wherein the compound is selected from the group consisting of:

6-(4-((1s,3s)-1-amino-3-hydroxy-3-methylcyclobutyl)phenyl)-5-phenyl-3-(2,2,2-trifluoroethyl)furo[2,3-d]pyrimidin-4(3H)-one;

6-(4-((1r,3r)-1-amino-3-hydroxy-3-methylcyclobutyl)phenyl)-5-phenyl-3-(2,2,2-trifluoroethyl)thieno[2,3-d]pyrimidin-4(3H)-one; and 6-(4-((1r,3r)-1-amino-3-hydroxy-3-methylcyclobutyl)phenyl)-7-methyl-5-phenyl-3-(2,2,2-trifluoroethyl)-3H-pyrrolo[2,3-d]pyrimidin-4(7H)-one;

or a pharmaceutically acceptable salt, stereoisomer or tautomer thereof.

19. The compound of claim 1, wherein the compound is 6-(4-((1 s,3 s)-1-amino-3-hydroxy-3-methylcyclobutyl)phenyl)-5-phenyl-3-(2,2,2-trifluoroethyl)furo[2,3-d]pyrimidin-4(3H)-one, or a pharmaceutically acceptable salt, stereoisomer or tautomer thereof.

20. A pharmaceutical composition comprising a pharmaceutical carrier, and a compound of claim 1.

21. A method of treating cancer comprising administering a compound according to claim 1 to a subject in need thereof, wherein the cancer is selected from the group consisting of prostate cancer, breast cancer, and ovarian cancer.

22. A pharmaceutical composition comprising a pharmaceutical carrier, and a compound of claim 16.

23. A method of treating cancer comprising administering a compound according to claim 16 to a subject in need thereof, wherein the cancer is selected from the group consisting of prostate cancer, breast cancer, and ovarian cancer.

* * * * *